US012699084B2

(12) United States Patent
Weiss et al.

(10) Patent No.: US 12,699,084 B2
(45) Date of Patent: Aug. 4, 2026

(54) METHOD AND MEANS FOR DIAGNOSING A HUMAN SEPSIS

(71) Applicant: Julius-Maximilans-Universität Würzburg, Würzburg (DE)

(72) Inventors: Lukas Weiss, Veitsbronn (DE); Georgi Manukjan, Hannover (DE); Dirk Weismann, Zellingen (DE); Harald Schulze, Margetshöchheim (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 1215 days.

(21) Appl. No.: 17/633,632

(22) PCT Filed: Aug. 10, 2020

(86) PCT No.: PCT/EP2020/072409
§ 371 (c)(1),
(2) Date: Feb. 8, 2022

(87) PCT Pub. No.: WO2021/023894
PCT Pub. Date: Feb. 11, 2021

(65) Prior Publication Data
US 2022/0412960 A1     Dec. 29, 2022

(30) Foreign Application Priority Data

Aug. 8, 2019    (EP) ..................................... 19190817

(51) Int. Cl.
*G01N 33/50*        (2006.01)
*G01N 33/569*       (2006.01)
(52) U.S. Cl.
CPC ..... *G01N 33/5091* (2013.01); *G01N 33/5094* (2013.01); *G01N 33/56966* (2013.01); *G01N 2800/26* (2013.01)

(58) Field of Classification Search
CPC ........... G01N 33/5091; G01N 33/5094; G01N 33/56966; G01N 33/6893; G01N 33/86; G01N 2800/26
See application file for complete search history.

(56) References Cited

U.S. PATENT DOCUMENTS

2013/0203175 A1     8/2013   Xu et al.
2014/0363423 A1*   12/2014   Huang ..................... C07K 7/06
                                                                    514/19.2

FOREIGN PATENT DOCUMENTS

WO        2015138441 A1      9/2015
WO        2016100103 A1      6/2016
WO        2019006561 A1      1/2019

OTHER PUBLICATIONS

Claushuis et al. Different roles of platelet glycoprotein VI and CLEC2 during gram negative pneumonia derived sepsis. Research and Practice in Thrombosis and Haemostasis. vol. 1, Supp. Supplement 1, pp. 114-115: Abstract: OC 56.1 (Jul. 2017).*

(Continued)

*Primary Examiner* — Gailene Gabel
(74) *Attorney, Agent, or Firm* — SALIWANCHIK, LLOYD & EISENSCHENK

(57)                    ABSTRACT

The present invention relates to a method of diagnosing a human sepsis. The present invention further relates to a kit for diagnosing a human sepsis. The present invention also relates to a point-of-care device for performing a method of diagnosing a human sepsis. The present invention also relates to a use of a kit and/or a point-of-care device for a method of diagnosing a human sepsis. The present invention also relates to the use of a kit and/or a point-of-care device for a method of diagnosing a human sepsis. The method comprises stimulating a platelet-specific (hem-)ITAM receptor by adding a (hem-)ITAM receptor agonistic agent to a blood sample of a patient, wherein said agonistic agent (Continued)

comprises CRP-XL and/or convulxin, and measuring a platelet function level.

15 Claims, 17 Drawing Sheets

Specification includes a Sequence Listing.

(56) References Cited

OTHER PUBLICATIONS

Deppermann, Carsten. Platelets and vascular integrity. Platelets 29 (6): 549-555 (2018).*

Claushuis et al. Platelet glycoprotein VI aids in local immunity during pneumonia-derived sepsis caused by gram-negative bacteria. Blood 131 (8): 864-876 (Feb. 22, 2018).*

Martyanov et al. CLEC-2- Induced Signaling in Blood Platelets. Biochemistry (Moscow) Supplement Series B: Biomedical Chemistry 13 (1): 26-35 (Jan. 1, 2019).*

Atkinson, B. T., et al. "Signalling events underlying platelet aggregation induced by the glycoprotein VI agonist convulxin." European journal of biochemistry 268.20 (2001): pp. 5242-5248.

Waller, A. K., et al. "Flow cytometry for near-patient testing in premature neonates reveals variation in platelet function: a novel approach to guide platelet transfusion." Pediatric Research 85.6 (2019): pp. 874-884.

* cited by examiner

A

B

C

D

A

B

C

D

E

F

A

B

C

A

B

SEQUENCE LISTING

```
<160> NUMBER OF SEQ ID NOS: 3

<210> SEQ ID NO 1
<211> LENGTH: 37
<212> TYPE: PRT
<213> ORGANISM: Artificial Sequence
<220> FEATURE:
<223> OTHER INFORMATION: CRP-XL
<220> FEATURE:
<221> NAME/KEY: MOD_RES
<222> LOCATION: (3)..(3)
<223> OTHER INFORMATION: X/Xaa is L-4-hydroxyproline; 4Hyp
<220> FEATURE:
<221> NAME/KEY: MOD_RES
<222> LOCATION: (6)..(6)
<223> OTHER INFORMATION: X/Xaa is L-4-hydroxyproline; 4Hyp
<220> FEATURE:
<221> NAME/KEY: MOD_RES
<222> LOCATION: (9)..(9)
<223> OTHER INFORMATION: X/Xaa is L-4-hydroxyproline; 4Hyp
<220> FEATURE:
<221> NAME/KEY: MOD_RES
<222> LOCATION: (12)..(12)
<223> OTHER INFORMATION: X/Xaa is L-4-hydroxyproline; 4Hyp
<220> FEATURE:
<221> NAME/KEY: MOD_RES
<222> LOCATION: (15)..(15)
<223> OTHER INFORMATION: X/Xaa is L-4-hydroxyproline; 4Hyp
<220> FEATURE:
<221> NAME/KEY: MOD_RES
<222> LOCATION: (18)..(18)
<223> OTHER INFORMATION: X/Xaa is L-4-hydroxyproline; 4Hyp
<220> FEATURE:
<221> NAME/KEY: MOD_RES
<222> LOCATION: (21)..(21)
<223> OTHER INFORMATION: X/Xaa is L-4-hydroxyproline; 4Hyp
<220> FEATURE:
<221> NAME/KEY: MOD_RES
<222> LOCATION: (24)..(24)
<223> OTHER INFORMATION: X/Xaa is L-4-hydroxyproline; 4Hyp
<220> FEATURE:
<221> NAME/KEY: MOD_RES
<222> LOCATION: (27)..(27)
<223> OTHER INFORMATION: X/Xaa is L-4-hydroxyproline; 4Hyp
<220> FEATURE:
<221> NAME/KEY: MOD_RES
<222> LOCATION: (30)..(30)
<223> OTHER INFORMATION: X/Xaa is L-4-hydroxyproline; 4Hyp
<220> FEATURE:
<221> NAME/KEY: MOD_RES
<222> LOCATION: (33)..(33)
<223> OTHER INFORMATION: X/Xaa is L-4-hydroxyproline; 4Hyp
<220> FEATURE:
<221> NAME/KEY: MOD_RES
<222> LOCATION: (36)..(36)
<223> OTHER INFORMATION: X/Xaa is L-4-hydroxyproline; 4Hyp

<400> SEQUENCE: 1

Gly Lys Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Lys Xaa Gly
        35
```

<210> SEQ ID NO 2
<211> LENGTH: 158
<212> TYPE: PRT
<213> ORGANISM: Crotalus durissus terrificus

<400> SEQUENCE: 2

Met Gly Arg Phe Ile Phe Val Ser Phe Gly Leu Leu Val Leu Phe Leu
1               5                   10                  15

Ser Leu Ser Gly Thr Gly Ala Gly Leu His Cys Pro Ser Asp Trp Tyr
            20                  25                  30

Tyr Tyr Asp Gln His Cys Tyr Arg Ile Phe Asn Glu Glu Met Asn Trp
        35                  40                  45

Glu Asp Ala Glu Trp Phe Cys Thr Lys Gln Ala Lys Gly Ala His Leu
    50                  55                  60

Val Ser Ile Lys Ser Ala Lys Glu Ala Asp Phe Val Ala Trp Met Val
65                  70                  75                  80

Thr Gln Asn Ile Glu Glu Ser Phe Ser His Val Ser Ile Gly Leu Arg
                85                  90                  95

Val Gln Asn Lys Glu Lys Gln Cys Ser Thr Lys Trp Ser Asp Gly Ser
            100                 105                 110

Ser Val Ser Tyr Asp Asn Leu Leu Asp Leu Tyr Ile Thr Lys Cys Ser
        115                 120                 125

Leu Leu Lys Lys Glu Thr Gly Phe Arg Lys Trp Phe Val Ala Ser Cys
    130                 135                 140

Ile Gly Lys Ile Pro Phe Val Cys Lys Phe Pro Pro Gln Cys
145                 150                 155

<210> SEQ ID NO 3
<211> LENGTH: 148
<212> TYPE: PRT
<213> ORGANISM: Crotalus durissus terrificus

<400> SEQUENCE: 3

Met Gly Arg Phe Ile Phe Val Ser Phe Gly Leu Leu Val Val Phe Leu
1               5                   10                  15

Ser Leu Ser Gly Ser Glu Ala Gly Phe Cys Cys Pro Ser His Trp Ser
            20                  25                  30

Ser Tyr Asp Arg Tyr Cys Tyr Lys Val Phe Lys Gln Glu Met Thr Trp
        35                  40                  45

Ala Asp Ala Glu Lys Phe Cys Thr Gln Gln His Thr Gly Ser His Leu
    50                  55                  60

Val Ser Phe His Ser Thr Glu Glu Val Asp Phe Val Val Lys Met Thr
65                  70                  75                  80

His Gln Ser Leu Lys Ser Thr Phe Phe Trp Ile Gly Ala Asn Asn Ile
                85                  90                  95

Trp Asn Lys Cys Asn Trp Gln Trp Ser Asp Gly Thr Lys Pro Glu Tyr
            100                 105                 110

Lys Glu Trp His Glu Glu Phe Glu Cys Leu Ile Ser Arg Thr Phe Asp
        115                 120                 125

Asn Gln Trp Leu Ser Ala Pro Cys Ser Asp Thr Tyr Ser Phe Val Cys
    130                 135                 140

Lys Phe Glu Ala
145

METHOD AND MEANS FOR DIAGNOSING A HUMAN SEPSIS

CROSS REFERENCE TO RELATED APPLICATIONS

This application is a National Stage Application of International Application Number PCT/EP2020/072409, filed Aug. 10, 2020; which claims priority to European Patent Application No. 19190817.7, filed Aug. 8, 2019.

The Sequence Listing for this application is labeled "SeqList-14Dec21-ST25.txt", which was created on Dec. 14, 2021 and is 5 KB. The entire content is incorporated herein by reference in its entirety.

FIELD OF THE INVENTION

The present invention relates to a method of diagnosing a human sepsis. The present invention further relates to a kit for diagnosing a human sepsis. The present invention also relates to a point-of-care device for performing a method of diagnosing a human sepsis. The present invention also relates to a use of a kit and/or a point-of-care device for a method of diagnosing a human sepsis.

BACKGROUND OF THE INVENTION

With approximately 30 million cases per year and an in-hospital mortality of 20% to 40% sepsis and septic shock comprise a major health-burden. Improved pathophysiological understanding of sepsis has resulted in a recently updated definition of sepsis and septic shock, which are now defined as clinical syndromes based on organ failure and shock, accounted for by the sepsis-related organ failure assessment score (SOFA score). The basis of a sepsis diagnosis is commonly an infection and an increase in the SOFA score.

An early diagnosis and immediate start of an antibiotic therapy is crucial for patient survival. It has been reported that mortality increases by 7.6% within every hour without therapy initiation after hypotension onset. As an integral part of the SOFA score, low platelet count is an important laboratory finding for diagnosing sepsis.

Thrombocytopenia is an integral part of the SOFA score, which is essential for sepsis diagnosis, and is associated with poor prognosis. However, initial sepsis symptoms may be unspecific, and platelet count may not decrease until the disease progresses. In addition to the platelet count, dysregulated platelet function is also physiologically relevant for sepsis progression. Currently, markers for the early diagnosis of sepsis or the risk of sepsis are lacking. However, only early markers would allow to identify sepsis or a risk of sepsis, before organ-failure or at least multi-organ failure is evident.

Platelets have a crucial role in infection and immunity. A loss of vascular integrity, mediated by platelets through sealing neutrophil-induced breaches within the vessel wall, leads to the formation of massive edema. This gatekeeper function depends mainly on the platelet immunoreceptors glycoprotein VI (GPVI) and C-type lectin-like receptor 2 (CLEC-2) expressed on platelets rather than on the total platelet count itself (Boulaftali et al. 2013 J Clin Invest).

GPVI is the main collagen receptor on platelets, with distinct binding sites for collagen and fibrin. C-type lectin 2 (CLEC-2) is a (hem-)ITAM receptor with podoplanin as a physiological ligand. Both receptors contain an immunoreceptor tyrosine activating motif (ITAM) domain and participate in regulating the immune response during sepsis as recently investigated in several mouse models (Claushuis 2018 Blood, Rayes et al. 2017 Nat Commun).

While several recent investigations suggest a role of GPVI and CLEC-2 in mouse models of sepsis (Claushuis 2018 Blood, Rayes et al. 2017 Nat Commun, Hitchcock 2015 J Clin Invest), the exact role of these two (hem-)ITAM receptors remains controversial. Depending on the model used, the results with regard to the influence of the (hem-) ITAM receptors GPVI and CLEC-2 on sepsis disease progression were divergent. The present inventors thus studied the platelet function of human patients taking GPVI and CLEC-2 into account.

Woth 2013 describes a correlation between agonist-induced platelet aggregation and disease progression of sepsis, wherein a platelet function upon stimulation of GPVI with HORM collagen is investigated using aggregometry. However, HORM collagen does not bind selectively to GPVI, but also binds to other receptors.

Waller et al. 2019 report a method of diagnosing sepsis in newborns involving CRP-XL. However, a sepsis of newborns is different from a classical human sepsis in pathogen spectrum and pathophysiology. Furthermore, the platelet activity of newborns and humans older than 1 year old differs. The international statistic classification of diseases and related health problems classifies a classical human sepsis and a newborn sepsis as separate pathological conditions (classical human sepsis: A40, A41, R65.0, R65.1, R57.2; newborn sepsis: P36).

An early diagnosis of a sepsis is important to improve survival. The present invention aims at providing means to early diagnose and/or to monitor disease progression of sepsis in human adults, i.e. a patient having an age of >1 year, having a sepsis or being at risk of developing a sepsis. Furthermore, the present invention aims at assessing platelet function during a phase in which a patient has sepsis and/or during a phase in which a patient is at risk of acquiring a sepsis, such as by using flow cytometry, modified light transmission aggregometry (LTA), and/or immunoblot. The present invention further aims at providing easy-to-use means for quickly and efficiently diagnosing a sepsis, such as a kit for analyzing a blood sample of a patient having a sepsis or being at risk of acquiring a sepsis in a method of diagnosing, and a point-of-care device to be used in a method of diagnosing according to the present invention, and optionally said kit can be used with said point-of-care device.

The present inventors herein disclose that circulating platelets are not pre-activated during sepsis. Furthermore, the present inventors disclose that sepsis indicators such as the presence of thrombocytopenia, an increased immature platelet fraction, and/or an elevated GPVI-ectodomain plasma level occur unreliably when comparing different patients, partly days after intensive care unit (ICU) admission or not at all, and that these indicators do not correlate with disease severity. The present inventors further disclose that platelets are hyporeactive to several agonists and have a significant ITAM-receptor defect at ICU admission day and every patient during disease progression. The present inventors disclose that GPVI/ITAM receptor dysfunction is closely associated with bad outcome of a sepsis. Accordingly, the present inventors aim at providing a means capable of diagnosing sepsis at an early stage of disease progression by using the platelet function level after treatment with an agonist, preferably CRP-XL and/or convulxin, as in indicator of sepsis severity and/or an indicator of the risk of sepsis development.

SUMMARY OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the present invention relates to a method of diagnosing a human sepsis, comprising the following steps:

a) providing a blood sample of a patient, b) stimulating a platelet-specific (hem-)ITAM receptor by adding a (hem-)ITAM receptor agonistic agent to said sample, wherein said agonistic agent comprises CRP-XL and/or convulxin, c) measuring a platelet function level, wherein said patient has an age of >1 year.

In one embodiment, said sample is a whole blood sample, a platelet-rich plasma sample, a platelet suspension, or a platelet pellet.

In one embodiment, the level measured is compared to a reference value and/or a reference sample of a healthy person not suffering from sepsis.

In one embodiment, said method further comprises a step of determining that a patient has a sepsis or is at risk of developing a sepsis, if the platelet function level in said patient is decreased, in comparison to said reference value and/or said reference sample of a healthy person not suffering from sepsis.

In one embodiment, said agonistic agent comprises both CRP-XL and convulxin.

In one embodiment, said method is used for an early diagnosis of a sepsis.

In one embodiment, said platelet function level is characterized by at least one parameter selected from the group consisting of a surface presentation of P-selectin, an activated integrin $\alpha IIb/\beta 3$, a platelet aggregation, a mepacrine uptake/release, and a phosphorylation status of Syk, LAT, SHP-1, SHP-2, FcRy, and/or PLCy2.

In one embodiment, said measuring is performed by a method selected from flow cytometry, aggregometry, detection and quantification of nucleic acids by PCR or real time (quantitative) qPCR, ELISA, western blot, chromatography, and mepacrine assay.

In one embodiment, said measuring is performed by means of i) a flow cytometric analysis of a surface presentation of P-selectin, and/or of an activated integrin $\alpha IIb/\beta 3$, and/or mepacrine uptake/release, and/or ii) an aggregometry, and/or iii) a quantification of a phosphorylation status of Syk, LAT, SHP-1, SHP-2, FcRy, and/or PLCy2.

In one embodiment, said measuring is performed by means of at least one of i), at least one of ii), and at least one of iii).

In one embodiment, said measuring is performed by means of i), ii), and iii).

In one embodiment, said flow cytometric analysis of a surface presentation of P-selectin is performed using an antibody against a P-selectin, preferably an anti-CD62P antibody, and/or said flow cytometric analysis of an activated integrin $\alpha IIb/\beta 3$ is performed using an antibody against an activated conformation of integrin $\alpha IIb/\beta 3$, preferably the PAC-1 antibody, by fluorophore-conjugated fibrinogen, or other antibodies recognizing the activated conformation of $\alpha IIb/\beta 3$, wherein a decreased binding of said antibody against P-selectin and/or said antibody against an activated conformation of integrin $\alpha IIb/\beta 3$ is an indicator for sepsis, compared to a reference value and/or a reference sample of a healthy person not suffering from sepsis.

In one embodiment, said aggregometry is performed by any of light transmission aggregometry, impedance aggregometry, multiple electrode aggregometry, lumino-aggregometry, and microscale aggregometry, wherein a decreased aggregation of platelets is an indicator for sepsis, compared to a reference value and/or a reference sample of a healthy person not suffering from sepsis.

In one embodiment, said quantification of a phosphorylation status is performed by western blot using an antibody against phosphorylated Syk, phosphorylated LAT, phosphorylated SHP-1, phosphorylated SHP-2, phosphorylated FcRy, and/or phosphorylated PLCy2, preferably against phosphorylated Syk (Y525/526) and/or phosphorylated LAT (Y191), wherein a hypophosphorylation is an indicator for sepsis, compared to a reference value and/or a reference sample of a healthy person not suffering from sepsis.

In one embodiment, said method is used for monitoring a patient's health condition, wherein said monitoring comprises performing steps a)-c) at a time point $t_1$ and a time point $t_2$, or wherein said monitoring comprises performing step a) at a time point $t_1$ and a time point $t_2$, and performing steps b)-c) subsequent to performing said step a) at said time point $t_2$, wherein said time point $t_2$ is after said time point $t_1$.

In one embodiment, an increase in the platelet function level from said time point $t_1$ to said time point $t_2$ indicates an amelioration of the patient's health condition or wherein a decrease in the platelet function level from said time point $t_1$ to said time point $t_2$ indicates a worsening of the patient's health condition.

In one embodiment, a time interval between said time point $t_1$ and said time point $t_2$ is preferably in the range between 6 h and 7 days, more preferably 1 day to 2 days.

In a further aspect, the present invention relates to a kit for diagnosing a human sepsis comprising a container containing an agonistic agent for stimulating a platelet-specific (hem-)ITAM receptor, said agonistic agent comprising CRP-XL and/or convulxin, optionally auxiliary compounds for performing the method as defined above, optionally comprising instructions for diagnosing a human sepsis, particularly for comparing a platelet function level of a patient to a reference value and/or a reference sample of a healthy person not suffering from sepsis, wherein a decrease in the platelet function level indicates a human sepsis.

In this aspect, said diagnosing, said human sepsis, said agonistic agent, said stimulating, said method, said platelet function level, said patient, said reference value and/or reference sample, and said decrease are as defined above.

In a further aspect, the present invention relates to a point-of-care device for performing the method of diagnosing a human sepsis as defined above, comprising:

a sample inlet an analyzing unit an evaluation unit comprising a detector capable of detecting a platelet function level, wherein said detector generates an output signal indicating a level of platelet function.

In this aspect, said method, said diagnosing, said sepsis, said sample, and said platelet function level are as defined above.

In a further aspect, the present invention relates to a use of a kit, as defined above, or a point-of-care device, as defined above, for a method of diagnosing a human sepsis, as defined above.

In a further aspect, the present invention also relates to a use of CRP-XL and/or convulxin for the manufacture of a (hem-)ITAM receptor agonistic agent for diagnosing a human sepsis.

In this aspect, said CRP-XL, said convulxin, said agonistic agent, said diagnosing, and said sepsis, are as defined above.

In a further aspect, the present invention also relates to a method of treatment of sepsis comprising monitoring and/or diagnosing said sepsis using a method of diagnosing a human sepsis as defined above.

In this aspect, said sepsis and said method of diagnosing are as defined above.

DETAILED DESCRIPTION

The present invention relates to a diagnostic and prognostic test for sepsis which is based on an analysis of platelet function. Particularly, the present invention relates to a method of diagnosing a sepsis, which corresponds to such a diagnostic and prognostic test, comprising stimulating platelets with an agonistic agent comprising CRP-XL and/or convulxin, and measuring the platelet function level in response to the stimulation. Furthermore, the present invention relates to a kit, a point-of-care device, and a use of said kit and/or said point-of-care device for carrying out a method of diagnosing of the present invention.

A method of the present invention is based on the observation that, in sepsis patients, the function of platelets upon stimulation with a (hem-)ITAM receptor agonist is disturbed compared to a healthy individual.

The term "diagnosis" or "diagnosing", as used herein, relates to inspecting a patient's health condition, preferably relates to determining which disease or condition causes a person's symptoms and/or health condition. In one embodiment, diagnosing relates to determining whether a person has a sepsis or is at risk of acquiring a sepsis.

The term "sepsis", "classical sepsis", or "human sepsis", as used herein, refers to a life-threatening condition that arises when the body's response to infection causes injury to its own tissues and organs. As used herein, the term "sepsis" does not refer to a neonatal sepsis. Common symptoms of a human sepsis include fever, increased heart rate, increased breathing rate, and confusion. Symptoms of a sepsis may also include any of thrombocytopenia, hyperbilirubinemia, hypotension, fever, and tachypnea. A patient may have a septic shock characterized by low blood pressure due to sepsis that does not improve after fluid replacement. Sepsis is caused by inflammatory immune responses triggered by an infection, such as a bacterial infection. Sepsis may also be caused by an infection with a fungal pathogen, a virus, or a protozoan. The risk of acquiring a sepsis is increased with old age, a weakened immune system due to conditions such as cancer or diabetes, major trauma, or burns. Sepsis is commonly treated with intravenous fluids and antibiotics. According to systemic inflammatory response syndrome (SIRS) criteria, there were different levels of sepsis: sepsis, severe sepsis, and septic shock. SIRS is the presence of two or more of the following: abnormal body temperature, heart rate, respiratory rate, or blood gas, and white blood cell count. In one embodiment, a patient having sepsis has an age >1 year, and said sepsis is not a neonatal sepsis. In one embodiment, a sepsis diagnosed with a method of the present invention is a sepsis caused by a pathogen selected from *Staphylococcus aureus, Escherichia coli, Pseudomonas aeruginosa, Klebsiella* species. The present invention does not relate to diagnosing a neonatal sepsis of a patient having an age <1 year which may be caused by, for example, group 5 *Streptococcus, E. Coli*, Coagulase-Negative Staphylococci, and/or *Staphylococcus aureus*. In one embodiment, the basal thrombocyte function of neonates is diminished compared to the basal thrombocyte function of adults and children having an age >1 year, and the basal level of von Willebrand factor is increased in neonates compared to the basal level of von Willebrand factor in adults and children having an age >1 year (Andres et al. 2015 Thromb Haemost). In one embodiment, a sepsis of neonates and a sepsis of adults/children having an age >1 year differ due to the above mentioned difference in the basal levels of thrombocyte function and the above mentioned difference in the basal levels of von Willebrand factor.

The term "SOFA score", as used herein, relates to a sepsis-related organ failure assessment score which is sometimes also referred to as sequential organ failure assessment score. The SOFA score is used to grade the health condition of a patient having a sepsis. The score takes into account six different scores, one each for the respiratory, cardiovascular, hepatic, coagulation, renal and neurological systems.

The term "blood sample", as used herein, refers to sample of a patient which is blood and/or comprises blood of said patient. In one embodiment, blood relates to whole blood, platelet-rich plasma, a platelet suspension, or a platelet pellet. In one embodiment, a platelet pellet is a pellet derived from centrifugation of whole blood and/or platelet-rich plasma. In one embodiment, a platelet suspension is a suspension of pellets in HEPES-buffered Tyrode's solution. In a preferred embodiment, prior to an analysis of a blood sample, said blood sample is split into at least two aliquots, wherein one aliquot is to be stimulated with CRP-XL and one aliquot is to be stimulated with convulxin. In an alternative preferred embodiment, a blood sample is stimulated with both CRP-XL and convulxin. One advantage of the present invention is that a method of diagnosing according to the present invention can be performed using only very small amounts of blood, such as 10-15 μl.

The term "patient", as used herein, relates to a subject which has a sepsis or which is at risk of acquiring a sepsis. When referring to a patient in the context of the present invention, the patient is at least 1 year old. In one embodiment, a patient having a sepsis or being at risk of acquiring a sepsis is not a neonatal patient having a neonatal sepsis or being at risk of acquiring a neonatal sepsis.

The term "stimulating", as used herein, refers to treating a target with an agent, such as treating a receptor with an agonistic agent. In one embodiment, said stimulating with an agent induces an effect in said target. In one embodiment, a platelet-specific (hem-)ITAM receptor is stimulated with a (hem-)ITAM receptor agonistic agent, said agonistic agent preferably comprising CRP-XL and/or convulxin. Said stimulation typically results in dimerization and clustering of GPVI, followed by phosphorylation of signalling proteins such as FcRy, Syk, LAT, and/or PLCy2. Typically, said phosphorylation of signalling proteins mediates calcium mobilization, activation of platelet surface integrins, such as glycoprotein IIb/IIIa, and exocytosis of alpha and delta granules.

The term "(hem-)ITAM receptor" or "(hem-)ITAM immunoreceptor", as used herein, relates to a receptor involving an immunoreceptor tyrosine-based activation motif (ITAM). ITAM is a conserved sequence of four amino acids that is typically repeated twice in the cytoplasmic parts of certain cell surface proteins of the immune system. The motif contains a tyrosine separated from a leucine or iso-leucine by any two other amino acids. Typically, an ITAM receptor comprises two of these motifs which are separated by 6 to 12 amino acids. In one embodiment, GPVI is an ITAM receptor comprising two of these motifs. CLEC-2 comprises only one of these motifs and is thus called a hem-ITAM receptor. When referring to a "(hem-)ITAM receptor" in the context of the present invention, an ITAM receptor (typically comprising two motifs) and/or a hem-ITAM receptor (typically comprising one motif) is meant. In one embodiment, glycoprotein VI (GPVI) and CLEC-2 are (hem-)ITAM immunoreceptors which are expressed on platelets. In one embodiment, GPVI and CLEC-2 are (hem-)ITAM immunoreceptors, associated with a FcRy chain, which transduces the stimulatory signal via Src family kinases and Syk to the LAT signalosome and PLCy2, resulting in calcium influx and platelet activation. GPVI is a receptor stimulated by collagen as well as by collagen-related peptide cross-linked (CRP-$X_L$). CLEC-2 is a receptor which is activated by podoplanin as well as rhodocytin. In one embodiment, a (hem-)ITAM receptor is preferably GPVI and/or CLEC-2.

The term "agonistic agent" or "agonist", as used herein, refers to a chemical that binds to a receptor and activates the receptor to produce a biological response, and/or a chemical composition comprising at least one type of said chemical. In one embodiment, an agonistic agent is a composition comprising CRP-XL and/or convulxin. In one embodiment, an agonistic agent is CRP-XL or convulxin. In one embodiment, CRP-XL is an agonist of GPVI and/or convulxin is an agonist of GPVI. In one embodiment, an agonistic agent stimulates a platelet-specific (hem-)ITAM receptor.

The term "CRP-XL", as used herein, relates to a collagen-related peptide that is a selective, synthetic agonist which stimulates GPVI. In one embodiment, the term "CRP-XL" is used synonymously with cross-linked collagen related peptide. CRP-XL comprises cross-linked lysine residues. In one embodiment, CRP-XL has an amino acid sequence of SEQ ID NO. 1, namely amino acid sequence GKXGPXGPXGPXGPXGPXGPXGPXGPXGPXG-KXG, in which X is L-4-hydroxyproline. In one embodiment, CRP-XL is cross-linked using glutaraldehyde. In one embodiment, a derivative and/or fragment of CRP-XL may be used to stimulate a blood sample, wherein said derivative and/or fragment comprise(s) at least two glycine-proline-hydroxyproline sequences. The term "convulxin", as used herein, refers to a snake venom toxin found in a rattlesnake, particularly rattlesnake *Crotalus durissus terrificus*. Convulxin causes platelet activation in the blood forming clots. Convulxin acts as an agonist to the GPVI receptor, which is a major signalling receptor for collagen. In one embodiment, convulxin is a tetramer of heterodimers of an alpha and a beta subunit, i.e. (alpha/beta)$_4$. In one embodiment, said alpha subunit of convulxin has an amino acid sequence of SEQ ID NO. 2, namely MGRFIFVSFGLLVLFLSLSGT-GAGLHCPSDWYYYDQHCYRIFNEEMNWEDAEWF-CTKQAK GAHLVSIKSAKEADFVAWMVTQNIEESFS-HVSIGLRVQNKEKQCSTKWSDGSSVSYDNLLD LYITKCSLLKKETGFRKWFVASCIGKIPFVCKFPPQC, and said beta subunit has an amino acid sequence of SEQ ID NO. 3, namely MGRFIFVSFGLLVVFLSLSGSEAGFCCP-SHWSSYDRYCYKVFKQEMTWADAEKFCTQQHTG SHLVSFHSTEEVDFVVKMTHQSLKSTFFWIGAN-NIWNKCNWQWSDGTKPEYKEWHEEFE CLIS-RTFDNQWLSAPCSDTYSFVCKFEA.

The term "measuring", as used herein, relates to quantifying a parameter in a sample, such as quantifying a platelet function level. In one embodiment, measuring of a platelet function level is performed using any method, preferably any of the methods of flow cytometry, aggregometry, detection and quantification of nucleic acids by PCR or real time (quantitative) qPCR, ELISA, microscopy such as immunofluorescence microscopy, western blot, mass spectrometry, chromatography, and mepacrine assay. In one embodiment, a mepacrine assay comprises measuring uptake/release of mepacrine by platelets which can be performed by determining the end point or by performing a kinetic method such as flow cytometry or fluorimetry. In one embodiment, a measurement is performed using flow cytometry and said measurement may analyze any parameter, including extracellular markers and intracellular markers, wherein said intracellular markers may relate to, for example, pSyk and pLAT. In one embodiment, said measuring of pSyk and/or pLAT may be performed analogously to a method of quantifying the intracellular phosphorylation of the cytoskeleton-associated vasodilator-stimulated phosphoprotein (VASP) by means of flow cytometry to study the efficacy of a therapy using P2Y12 inhibitors known to a person skilled in the art [Spurgeon et al. 2014, Mallouka et al. 2018]. In one embodiment, a platelet function level is measured by means of flow cytometric analysis of the phosphorylation of Syk, and/or LAT, and/or SHP-1, and/or SHP-2, and/or FcRy, and/or PLCy2. In one embodiment, a blood sample is measured within a period of time from about 30 min to 4 h after said blood sample is drawn from a patient. In one embodiment, an analysis of a blood sample occurs 30 min to 4 h after drawing said blood sample from a patient, which is in accordance with the guidelines of the International Society of Thrombosis and Haemostasis with regard to blood samples for platelet function analysis. In one embodiment, a sample is kept at room temperature until it is analyzed using a method of diagnosing a human sepsis of the present invention. In an alternative embodiment, a blood sample may be preserved after drawing said blood sample and analyzed at a later time point, for example the next day, i.e. a method of diagnosing a human sepsis may comprise a timely interruption. In case of an analysis using flow cytometry, such a timely interruption between drawing said sample and analyzing said sample may be performed by, for example, binding of an antibody such as a PAC-1 antibody and subsequent quenching with a buffer such as FACS-buffer. Such a timely interruption may optionally comprise a fixation using a compound such as paraformaldehyde and then interrupting the reaction, e.g. for up to 24 hours, prior to residual analysis steps. In case of an analysis comprising immunoblotting, a timely interruption may be performed after stopping the stimulation of a sample with an agonistic agent using a lysis buffer, and optionally said sample may be stored at freezing temperatures such as −20° C. or −80° C. In case of an analysis comprising a mepacrine assay, a blood sample may be analyzed up to 48 h after drawing said blood sample from a patient. In a preferred embodiment, a blood sample is analyzed within 4 h after drawing said blood sample from a patient.

In one embodiment, when measuring a platelet function level using flow cytometry, the parameters analyzed are preferably presence of activated integrin αIIb/β3 and/or surface presentation of P-selectin after treatment with an agonistic agent. In one embodiment, when measuring a platelet function level by quantification of a phosphorylation status of Syk, LAT, SHP-1, SHP-2, FcRγ, and/or PLCγ2, the signal intensity of pSyk, pLAT, pSHP-1, pSHP-2, pFcRγ, and/or pPLCγ2, respectively, after treatment with an agonistic agent is measured. In one embodiment, when measuring a platelet function level by aggregometry, maximal aggregation in % is measured after treatment of a sample with an agonistic agent. In one embodiment, more than one measurement of a platelet function level of a blood sample can be performed using different methodologies, such as sequential measurements using aggregometry followed by immunoblot (FIG. 15).

The term "platelet function level", as used herein, refers to a measure that indicates the function and/or activation status of a platelet. Platelet function in a clinical setting is typically measured indirectly, for instance by in vitro bleeding time, using ADP/collagen or epinephrine/collagen cartridges. Characteristics of platelet activation are stimulation of different metabolic pathways, a shape change, activation of GP IIb/IIIa-receptors, and an induction of the procoagulant state. In one embodiment, the platelet function level, particularly a decrease in the platelet function level, is an indicator of whether a patient has a sepsis or is at risk of acquiring a sepsis. In one embodiment, the platelet function level is also an indicator of the reactivity of platelets towards an agonist. In one embodiment, the terms "platelet function" and "platelet function level" are used interchangeably.

The term "age of >1 year", as used herein, relates to an age of a patient who is older than 1 year old and who is thus not a neonatal patient (newborn patient).

The term "reference value and/or a reference sample", as used herein, refers to a control value and/or control sample which indicates the normal level of a parameter. In one embodiment, a reference value and a reference sample are a value detected in a healthy individual and a sample obtained from a healthy individual, respectively. In one embodiment, a reference value and/or reference sample is an indicator of an expected value identified in a healthy individual for a parameter of interest. In one embodiment, a reference value and/or reference sample allows to compare a value of a parameter detected in a patient with a value of said parameter expected for and/or detected in a healthy individual. In one embodiment, a reference sample is used to obtain a reference value. In one embodiment, a patient's platelet function level is compared to a reference value of a platelet function level, and a decreased platelet function level in said patient compared to said reference value indicates that said patient has a sepsis or is at risk of acquiring a sepsis. In one embodiment, a reference derives from a healthy person not suffering from sepsis. In one embodiment, the terms "reference" and "reference value and/or reference sample" are used interchangeably. In one embodiment, the term "comprising" may relate to "consisting of".

The term "early diagnosis", as used herein, refers to diagnosing a disease in an early stage of disease progression. In one embodiment, an early diagnosis of sepsis is a diagnosis of sepsis or a diagnosis of a risk of acquiring a sepsis, wherein said diagnosis occurs within 5 hours, preferably within 2 hours after patient admission. In one embodiment, an early diagnosis of sepsis is a diagnosis of sepsis within 6 hours, preferably within 2 hours of disease onset. In one embodiment, an early diagnosis of sepsis allows to detect a sepsis and/or a risk of acquiring a sepsis in a patient at least 6 hours, preferably at least 1 day, more preferably at least 1.5 days before the platelet count of said patient decreases below the reference value (<150/nL), said diagnosis involving detecting a decrease in the platelet function level. In one embodiment, a disease onset of sepsis is indicated, according to sepsis-3 criteria, by an infection and an increase in the SOFA score by at least two points above the baseline value, determined for each patient individually. General parameters indicating a sepsis are: fever (core temperature >38.3° C.), hypothermia (core temperature <36° C.), heart rate >90 bpm or >2 SD above the normal value for the age, tachypnea: >30 bpm, hyperventilation ($pCO_2 \leq 32$ mmHg), altered mental status, significant edema or positive fluid balance (>20 ml/kg over 24 h), and/or hyperglycemia (plasma glucose >110 mg/dl or 7.7 mM/1) in the absence of diabetes. Inflammatory parameters are leukocytosis (white blood cell count >12,000/μl), leukopenia (white blood cell count <4,000/μl), normal white blood cell count with >10% immature forms, plasma C reactive protein >2 SD above the normal value, and/or plasma procalcitonin >2 SD above the normal value. Hemodynamic parameters are arterial hypotension (systolic blood pressure <90 mmHg), mean arterial pressure <70, a systolic blood pressure decrease >40 mmHg in adults or <2 SD below normal for age), mixed venous oxygen saturation >70%, cardiac index >3.5 1 $min^{-1}$ $m^{-2c,d}$, organ dysfunction parameters, arterial hypoxemia (PaO2/FIO2<300), acute oliguria (urine output <0.5 ml $kg^{-1}$ $h^{-1}$ or 45 mM/l for at least 2 h), creatinine increase ≥0.5 mg/dl, coagulation abnormalities (international normalized ratio >1.5 or activated partial thromboplastin time >60 s). Further parameters are ileus (absent bowel sounds), thrombocytopenia (platelet count <100,000/μl), and hyperbilirubinemia (plasma total bilirubin >4 mg/dl or 70 mmol/l), as well as tissue perfusion parameters such as hyperlactatemia (>3 mmol/1). A common diagnosis tool for sepsis is the quick SOFA score (qSOFA) which indicates that a patient should be transferred to an intensive care unit if any two of the criteria i) tachypnoe >=22/min, ii) systolic blood pressure <=100 mmHg, and iii) disturbed vigilance (GCS<15; GCS: Glasgow-Coma Scale) are met.

The term "parameter", as used herein, relates to a certain feature of a system, such as a human body, that can be quantified and can be used to characterize said system. In one embodiment, said parameter is a parameter that characterizes the platelet function of a patient. In one embodiment, a parameter that is used to characterize platelet function is any of surface presentation of P-selectin, activated integrin αIIb/β3, platelet aggregation, mepacrine uptake/release, and phosphorylation status of Syk, LAT, SHP-1, SHP-2, FcRγ, and/or PLCγ2.

The term "P-selectin", as used herein, refers to a protein that functions as a cell adhesion molecule (CAM) on the surfaces of activated endothelial cells, which line the inner surface of blood vessels, and activated platelets. In inactivated platelets, P-selectin is stored in α-granules. In a quiescent platelet, P-selectin is located on the inner wall of α-granules. Platelet activation, e.g. by agonists such as thrombin, Type II collagen, or ADP, results in release of α- and dense granules, and the inner walls of the granules are exposed on the outside of the cell. The P-selectin then promotes platelet aggregation through platelet-fibrin and platelet-platelet binding. In one embodiment, the presentation of P-selectin on the surface of platelets, herein referred to as "surface presentation", is an indicator and/or parameter of platelet function. P-selectin may also be called CD62P or Granule Membrane Protein 140 (GMP-140). In one embodiment, an increase in surface presentation of P-selectin is an indicator of platelet function. In one embodiment, stimulating a platelet with CRP-XL and/or convulxin increases surface presentation of P-selectin.

The term "integrin αIIb/β3", as used herein, relates to glycoprotein IIb/IIIa which is an integrin complex found on platelets. It is a receptor for fibrinogen and von Willebrand factor, and aids platelet activation. The complex is formed via calcium-dependent association of gpIIb and gpIIIa, a required step in normal platelet aggregation and endothelial adherence. In one embodiment, activated integrin αIIb/β3 is an indicator and/or parameter of platelet function. In one embodiment, an anti-Pac-1 antibody binds to activated integrin αIIb/β3, and a decreased binding of said antibody in a sample compared to a reference is an indicator of sepsis. In one embodiment, an activated integrin αIIb/β3 is measured by flow cytometry using an antibody that targets activated integrin αIIb/β3, or by using a fluorophore-labelled fibrinogen, or by using fluorescence microscopy.

The term "platelet aggregation", as used herein, refers to a process in which platelets aggregate. Platelet aggregation begins minutes after activation of the platelets, and occurs as a result of activation of GPIIb/IIIa receptors, allowing the receptors to bind with vWF or fibrinogen.

The term "phosphorylation status", as used herein, relates to a feature indicating whether a certain target protein, particularly a certain amino acid residue of a target protein, is phosphorylated or not. In one embodiment, a phosphorylation status indicates to what extend a target protein is phosphorylated. In one embodiment, the phosphorylation status of a target protein such as SYK, and/or of LAT, and/or of a SH2 domain of SHP-1 and/or SHP-2, and/or of FcRy, and/or of PLCy2 is determined, and a hypophosphorylation is an indicator for sepsis. In one embodiment, the phosphorylation status of at least one amino acid residue of a protein of the GPVI/CLEC2 signaling pathway, for example SYK, LAT, SHP-1, SHP-2, FcRy, and/or PLCy2, is determined, such as residues Y323 and Y525/526 of Syk, Y132, Y171, Y191, and Y226 of LAT, Y564 of SPH-1, as well as Y542 and Y580 of SHP-2. pSyk and pLAT refers to phosphorylated Syk and LAT, respectively. In one embodiment, decreased phosphorylation of Syk, LAT, SHP-1, SHP-2, FcRy, and/or PLCy2, compared to a reference value, is an indicator of the presence of a sepsis and/or a risk of acquiring a sepsis. In one embodiment, a phosphorylation status is quantified using western blot and/or an ELISA assay. In one embodiment, a phosphorylation status is quantified using densitometry after immunoblot (based on chemoluminescence), wherein a ratio of a phosphorylated target protein to an unphosphorylated target protein or to a housekeeping gene product is analyzed, such as pSyk/Syk and/or pSyk/housekeeping gene. In one embodiment, a quantification of a phosphorylation status involves analyzing a fluorescence of a fluorophore-coupled antibody. Within the context of the present invention, fluorescence can be measured by flow cytometry, by immunoblot or by ELISA. Horseradish peroxidase (HRP)-conjugated antibodies are typically used for chemoluminescence analysis (on films or by gel documentation analyzers). In an alternative embodiment, a quantification of a phosphorylation status involves mass spectrometry (analysis of a phospho-proteome) or CCD detection in fluorescence microscopy.

The term "spleen tyrosine kinase" or "Syk", as used herein, refers to an enzyme which in humans is encoded by the SYK gene and is a member of the Syk family of tyrosine kinases. The Syk family of tyrosine kinases are non-receptor cytoplasmic tyrosine kinases and share a characteristic dual SH2 domain separated by a linker domain.

The term "linker for the activation of T cells" or "LAT", as used herein, relates to a protein which is phosphorylated by ZAP70/Syk protein tyrosine kinases following activation of the T-cell antigen receptor (TCR) signal transduction pathway. LAT acts as a docking site for SH2 domain-containing proteins. Upon phosphorylation, LAT recruits multiple adaptor proteins and downstream signaling molecules into multimolecular signaling complexes located near the site of TCRs.

The terms "SHP-1" and "SHP-2" relate to "Src homology region 2 domain-containing phosphatase-1" and "Src homology region 2 domain-containing phosphatase-2", respectively. SHP-1 and SHP-2 belong to the protein tyrosine phosphatase (PTP) family.

The term "FcRy" relates to a Fc receptor (epsilon) gamma chain. FcRy belongs to the group of Fc receptors which bind to particular antibody subtypes.

The term "PLCy2" relates to phospholipase C gamma 2. PLCy2 is a phospholipase which cleaves phospholipids, particularly phosphatidylinositol.

The term "mepacrine uptake/release", as used herein, refers to an assay for measuring uptake and release of platelet dense granule contents using mepacrine. Preferably, mepacrine uptake and release by platelets is analyzed using flow cytometry, namely by measuring a fluorescence signal over time. In one embodiment, a mepacrine assay is performed as follows: mepacrine is added to a blood sample, preferably a diluted blood sample, followed by incubation for about 30 min at about 37° C. Then, a measurement is performed, for example for about seven minutes, using flow cytometry. The content of dense granules in the platelets is assessed by determining the mean fluorescence of mepacrine-loaded platelets minus the fluorescence of unloaded platelets. The discharging capacity of platelets is determined by the mepacrine signal intensity after stimulation with an agonist, e.g. for 5 min, minus the signal of mepacrine-loaded platelets. Mepacrine is accumulated in the membrane of dense granules and is released after stimulation due to the release of granules. A mepacrine uptake/release assay may also be performed as a kinetic mepacrine assay. In one embodiment, a mepacrine signal is measured using immunofluorescence microscopy by measuring a signal prior to stimulation and after stimulation of platelets. In one embodiment, a decreased mepacrine uptake and/or release is an indicator of a decreased platelet function level.

The term "aggregometry", as used herein, refers to a method of investigating aggregation of platelets. Platelet aggregometry is commonly applied in clinical settings to monitor a response to an antiplatelet therapy, to assess perioperative bleeding risk, or to diagnose inherited bleeding disorders. In one embodiment, aggregometry relates to any of light transmission aggregometry, impedance aggregometry, multiple electrode aggregometry, lumino-aggregometry, and microscale aggregometry. In one embodiment, a decreased aggregation of platelets is an indicator for sepsis and/or sepsis risk.

The term "releasate analysis", as used herein, relates to an analysis of components released by platelet degranulation, such as fibrinogen, vWF, serotonin, or platelet derived growth factor in the respective medium such as whole blood, blood plasma, or buffer.

The term "time point", as used herein, refers to a moment in time. In the context of the invention, a time point relates to a time point at which a sample is obtained from a patient. Typically, a sample is obtained at several time points, such as a time point $t_1$ and a time point $t_2$, and optionally more time points such as $t_3$, $t_4$, $t_5$, and so on. By comparing a platelet function level measured in an earlier sample (such as $t_1$) with a platelet function level measured in a later sample (such as $t_2$), it is possible to monitor a disease progression of sepsis. In one embodiment, an increase in the platelet function level from said earlier time point to said later time point indicates an amelioration of the patient's health condition, and a decrease in the platelet function level from said earlier time point to said later time point indicates a worsening of the patient's health condition, i.e. a manifestation of sepsis. In one embodiment, a time interval is an interval between an earlier time point and a later time point. In one embodiment, a time interval between obtaining a sample at an earlier time point and obtaining a sample at a later time point is in the range of from 1 h to 2 weeks, preferably in the range of from 6 h to 7 days, more preferably in the range of from 1 day to 2 days. In one embodiment, a preferred time interval between obtaining an earlier sample and a later sample is any time point according to the discretion of the treating physician, and may be, for example, one week between a first time point and a second time point.

The term "amelioration of the patient's health condition", as used herein, relates to a decrease in sepsis symptoms, such as a decrease in inflammation. In a case in which the health condition of a patient is monitored by measuring a platelet function level in blood samples of a patient obtained at subsequent time points, an amelioration of the patient's condition with regard to sepsis is indicated by an increase in the platelet function level from an earlier time point to a later time point. Furthermore, a worsening of the patient's health condition is indicated by a decrease in the platelet function level from an earlier time point to a later time point, which means that the patient is in the process of acquiring a sepsis and/or a sepsis of said patient becomes more severe.

The term "container", as used herein, relates to any container that is capable of containing and storing any substance needed in a kit such as a kit for diagnosing a human sepsis. In one embodiment, a container is also suitable to contain, and optionally store, a blood sample.

The term "auxiliary compounds", as used herein, refers to any compound that is useful in a kit for diagnosing a human sepsis. In one embodiment, an auxiliary compound may be, for example, a buffer such as FACS buffer, HEPES-buffered Tyrode's solution, or a modification thereof, an agonist such as ADP, collagen, and Thrombin Receptor Agonist Peptide (TRAP), an antibody such as a fluorescently labeled antibody. In one embodiment, a FACS buffer comprises or consists of phosphate-buffered saline with 0.1-1% bovine serum albumin.

The term "kit", as used herein, relates to a set of reagents that are necessary to perform a method of diagnosing a human sepsis according the invention. In one embodiment, a kit of the present invention is a kit that comprises all the components (other than the blood sample) necessary for carrying out a method of the present invention using flow cytometry as a measurement method. In one embodiment, when a kit is a kit to be used for flow cytometry, said kit comprises i) a platelet-specific antibody, such as an antibody for CD41, CD42$_a$, CD42b, CD42c/d, CD61, ii) a marker for platelet activation, iii) a buffer for diluting samples, such as modified Hepes-Tyrodes buffer, iv) a buffer for quenching the reaction, such as FACS buffer or modified Hepes- Tyrodes buffer, v) an agonistic agent. In one embodiment, when a kit is a kit to be used for aggregometry, said kit comprises i) an agonistic agent, ii) acetylsalicylic acid, iii) apyrase, iv) prostaglandin E1, v) a buffer for diluting a sample, such as modified Hepes-Tyrodes buffer, vi) $CaCl_2$. In one embodiment, when a kit is a kit to be used for quantifying a phosphorylation status, said kit comprises i) the components recited for a kit to be used for aggregometry, ii) lysis buffer and optionally components for performing a western blot, such as a PVDF or nitrocellulose membrane and blocking solution, iii) an antibody or antibody combination capable of detecting a phosphorylation status, preferably a combination of a pSyk and a Syk antibody, a pSyk and a housekeeping gene antibody, a pLAT and a LAT antibody, an antibody for any of phosphorylated targets FcRy, phosphorylated PLCy2, phosphorylated SHP-1, and phosphorylated SHP-2, and an antibody to the respective unphosphorylated target or a housekeeping gene antibody, and iv) a chemoluminescence reagent. In an alternative embodiment, when a kit is a kit to be used for quantifying a phosphorylation status using a flow cytometric analysis, said kit comprises i) a platelet-specific antibody, such as an antibody for CD41, CD42$_a$, CD42b, CD42c/d, CD61, ii) an agonistic agent, iii) modified Hepes-Tyrodes buffer, iv) an antibody specific for a phosphorylated epitope such an antibody for pSyk, pLAT, pSHP-1, pSHP-2, pFcRy, or pPLCy2. In one embodiment, when a kit is a kit to be used with more than one technique, a kit may comprise several or all off the above mentioned kit-related components, i.e. the components recited for a kit to be used for flow cytometry, and/or the components recited for a kit to be used for aggregometry, and/or the components recited for a kit to be used for quantifying a phosphorylation status. In one embodiment, a kit of the present invention can be used with a point-of-care device of the present invention to analyze a blood sample of a patient in a method of diagnosing of the present invention.

The term "point-of-care device", as used herein, refers to a device for medical diagnostic testing at or near the place of patient care. In one embodiment, a point-of-care device is used to analyze a blood sample of a patient, preferably blood that is anticoagulated with citrate. In one embodiment, a point-of-care device is used to analyze a blood sample, such as a whole blood sample, a platelet-rich plasma sample, a platelet suspension, or a platelet pellet. In one embodiment, the volume of blood analyzed in a single measurement performed with a point-of-care device is less than 1 ml. In one embodiment, the result of an analysis performed with a point-of-care device is available as soon as within one hour after the start of the analysis. In one embodiment, a point-of-care device is easy to handle and preferably cartridge-based. In one embodiment, a point-of-care device measures at least one parameter selected from a surface presentation of P-selectin, a presence of an activated integrin αIIb/β3, a platelet aggregation, mepacrine uptake and release, and a phosphorylation status of Syk, LAT, SHP-1, SHP-2, FcRy, and/or PLCy2. In one embodiment, a point-of-care device comprises a module for performing
  i) a flow cytometric analysis, such as of a surface presentation of P-selectin, and/or of an activated integrin αIIb/β3, and/or of mepacrine uptake/release, and/or a module for performing
  ii) an aggregometry, and/or a module for performing
  iii) a quantification of a phosphorylation status of Syk, LAT, SHP-1, SHP-2, FcRy, and/or PLCy2, and/or a module for performing any combination of i), ii), and iii), preferably a module for performing i) and iii)).

The term "sample inlet", as used herein, relates to an inlet for contacting a sample with a point-of-care (POC) device. In one embodiment, a sample inlet uses capillary force to contact a sample with a POC device. In one embodiment, the sample inlet receives the blood sample by means of injection, dipping, absorption, pressure, underinflation, vacuum, and/or capillary forces. In one embodiment, the sample inlet receives and transfers the blood sample to the analyzing unit.

The term "analyzing unit", as used herein, refers to a unit capable of analyzing a sample, e.g. by means of a measurement performed by a method selected from flow cytometry, aggregometry, detection and quantification of nucleic acids by PCR or real time (quantitative) qPCR, ELISA, western blot, chromatography, microscopy, and mepacrine assay. In one embodiment, an analyzing unit is preferably capable of i) a flow cytometric analysis of a surface presentation of P-selectin, and/or of an activated integrin $\alpha IIb/\beta3$, and/or ii) an aggregometry, and/or iii) a quantification of a phosphorylation status of Syk, LAT, SHP-1, SHP-2, FcRy, and/or PLCy2.

The term "evaluation unit", as used herein, refers to a unit that comprises a detector and which is able to detect the result of an analysis performed with an analyzing unit. In one embodiment, an evaluation unit detects a platelet function level and gives the result of said detection as an output signal. In one embodiment, an analyzing unit and evaluation unit may be comprised in one unit. In one embodiment, an analyzing unit is also capable of performing the function of an evaluation unit and/or an evaluation unit is also capable of performing the function of an analyzing unit.

The term "detector", as used herein, refers to a module that is capable of detecting a result of an analysis, such as detecting a platelet function level analyzed with any of flow cytometry, aggregometry, detection and quantification of nucleic acids by PCR or real time (quantitative) qPCR, ELISA, western blot, chromatography, microscopy, and mepacrine assay. In one embodiment, a detector generates an output signal indicating a platelet function level.

The term "output signal", as used herein, refers to a signal which indicates the result of an analysis, such as a quantified platelet function level.

BRIEF DESCRIPTION OF THE FIGURES

The present invention is now further described by reference to the following figures. All methods mentioned in the figure descriptions below were carried out as described in detail in the examples.

(A) Platelet count. (B) Reticulated platelets indicated as thiazole orange (TO) positive fraction were assessed by flow cytometry. (C) TPO levels in sepsis plasma were determined by ELISA. (D) Mean platelet volume. (E) Main platelet receptor and integrin expression was analyzed by flow cytometry in patients and corresponding healthy controls (HC). (F-I) Platelet (pre-)activation due to P-selectin exposure (CD62P) (F, G) and integrin $\alpha IIb\beta3$ activation (H, I) was assessed in whole blood measured by flow cytometry. Representative curves are shown in F and I. (A, B) Reference ranges are shown as dashed lines. (A-I) Graphs show median±IQR. Differences were analyzed using Wilcoxon matched-pairs signed rank test (A-C). Kolmogorov-Smirnov test (E). Kruskal-Wallis-test (B, G, I). n.s. non-significant, *p>0.05, p>0.01, *p>0.001, ****p>0.0001

Figure 3:
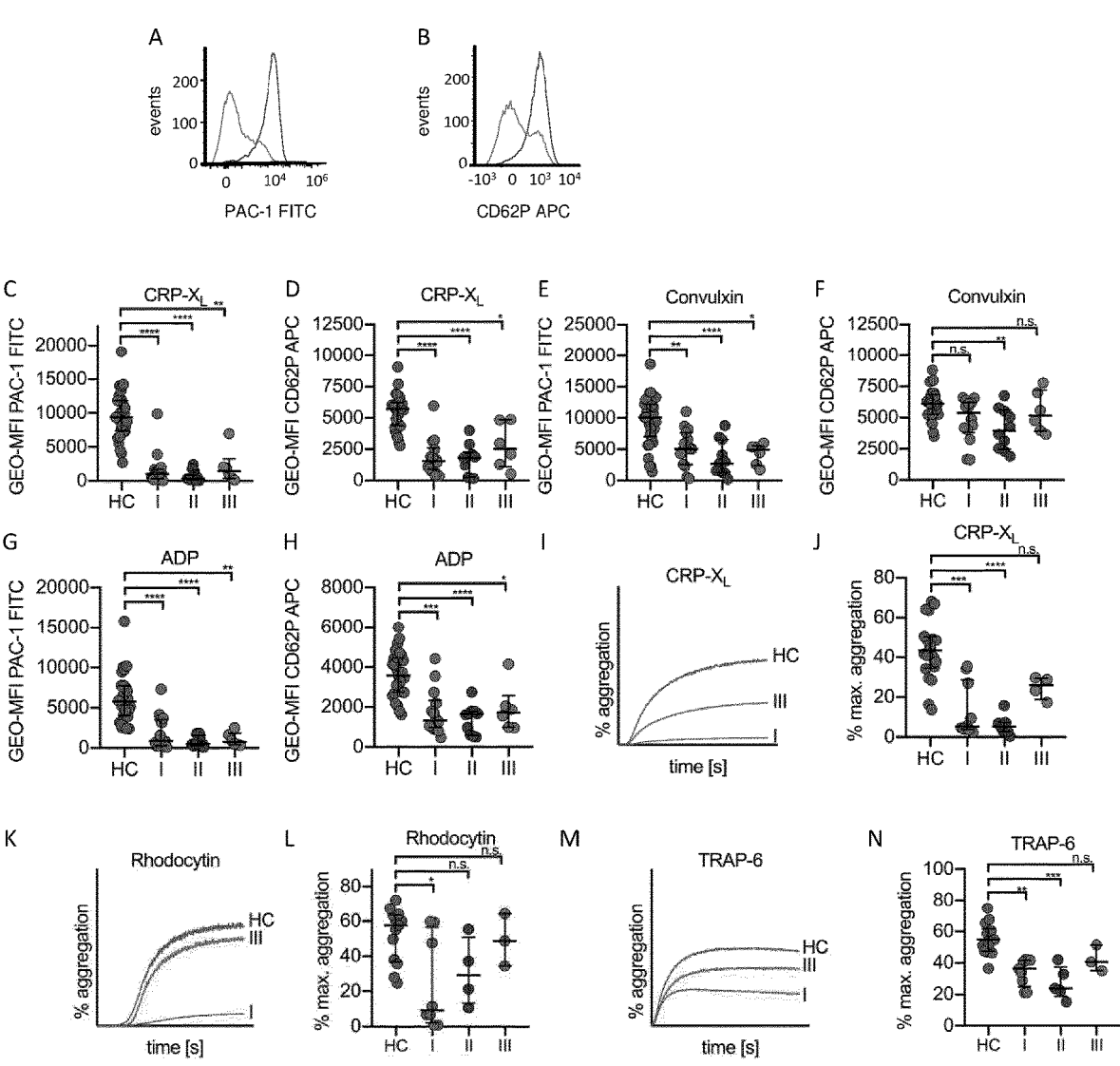

FIG. 3 shows that sepsis platelets are highly hyporeactive. Platelet reactivity assays are shown at the following time points: I: admission day, II: day 5-7 and III: day of ICU discharge. (S)=sepsis patient; (HC)=healthy control. (A-H) Platelet integrin activation (A, C, E, G) and P-selectin exposure (B, D, F, H) were measured upon stimulation with CRP-XL [0.01 µg/mL](A-D), Convulxin [0.01 µg/ml] (E, F) and ADP [5 µM] (G, H) in whole blood by flow cytometry. Representative curves upon CRP-XL stimulation at time point I are shown in A and B. (I-N) Light transmission aggregometry was performed using washed platelets [500 000 1/µL]. (I-N) Maximum aggregation is depicted upon stimulation with CRP-XL [0.1 µg/mL] (I, J) rhodocytin [1 nM] (K, L) and TRAP-6 [10 µM] (M, N). Representative curves are shown in FIG. I, K, M. CRP-XL samples were measured for 5 minutes, rhodocytin and TRAP-6 samples for 10 minutes. Graphs show median±IQR. Differences were analyzed by Kruskal-Wallis test (A-N). n.s. non-significant, *p>0.05, p>0.01, *p>0.001, ****p>0.0001

Figure 4:
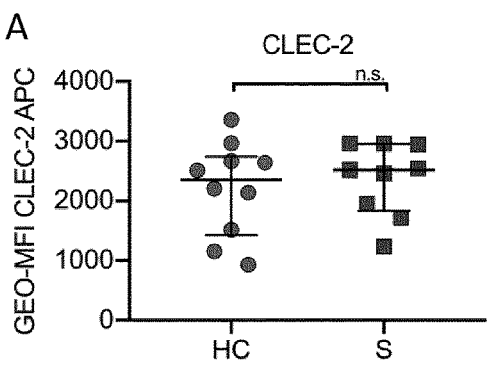
Figure 4:
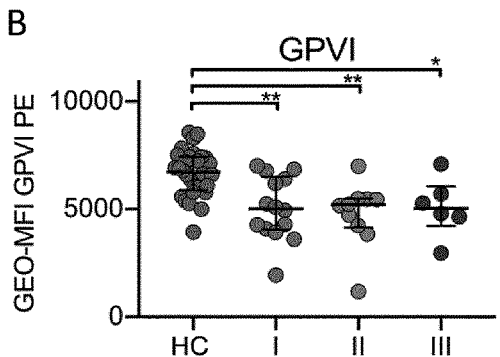
Figure 4:
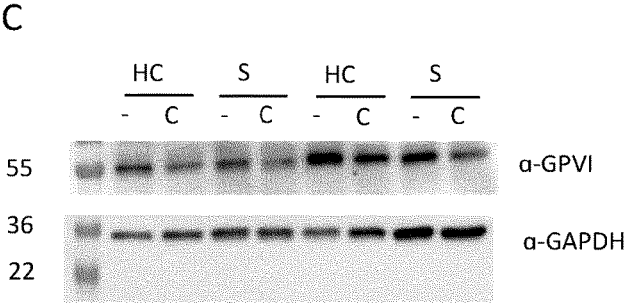
Figure 4:
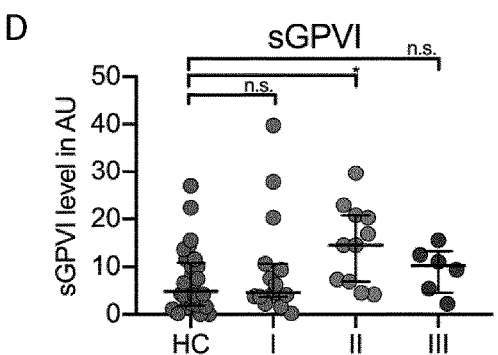

FIG. 4 shows that sepsis platelets show increased GPVI ectodomain shedding. Assays display the following time points: I: admission day, II: day 5-7 and III: day of ICU discharge). (S)=sepsis patient; (HC)=healthy control (A-B) CLEC-2 (A) and GPVI (B) expression on platelet surface were analyzed by flow cytometry (C) GPVI expression studied by Western blotting using JAQ-1 antibody. Platelet lysis was performed 60 minutes after stimulation with CRP-XL (C) [0.01 µg/mL] or under resting conditions (–) (D) ELISA for soluble GPVI ectodomain (sGPVI) was performed with plasma of sepsis patients and corresponding controls. Graphs show median±IQR. Differences were analyzed by Kolmogorov-Smirnov test (A) and Kruskal-Wallis test (B, D). n.s. non-significant, *p>0.05, **p>0.01.

Figure 5:
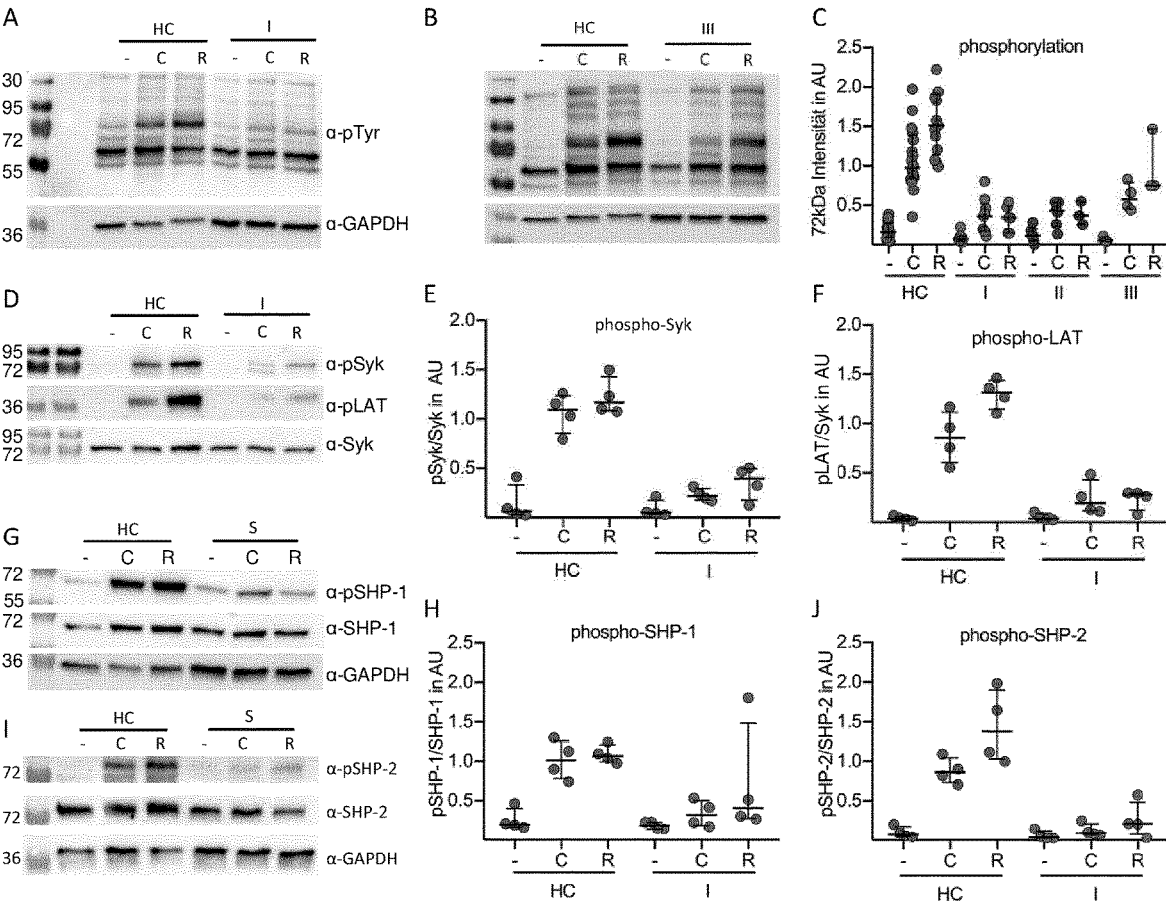

FIG. 5 shows that sepsis platelets show impaired (Hem-) ITAM Signaling. Washed platelets [500 000 1/µL] of healthy controls (HC) and patients (S) were stimulated with CRP-XL (C) and rhodocytin (R). Lysis was done at the following time points: C: 5 min, R: 10 min. I: admission day, II: day 5-7 and III: day of ICU discharge. (A-C) Western Blot analysis of platelet lysates. Staining was performed with anti-phospho-tyrosine antibody 4g10. 72 kDa band intensity was set in relation to signal intensity of Syk or GAPDH in arbitrary units (AU). Representative blots are shown in figures A (time point I) and B (time point III). (D-F) Phosphorylation of signaling peptides Syk and Lat was investigated by Western blot. One representative blot is shown in D. (G-J) Phosphorylation analysis of ITIM-signaling associated phosphatases SHP-1 and SHP-2. Phosphoprotein intensity was set in relation to intensity of unphosphorylated protein shown in H and J. Representative Western blots are shown in G and I. All graphs display median f IQR.

Figure 6:
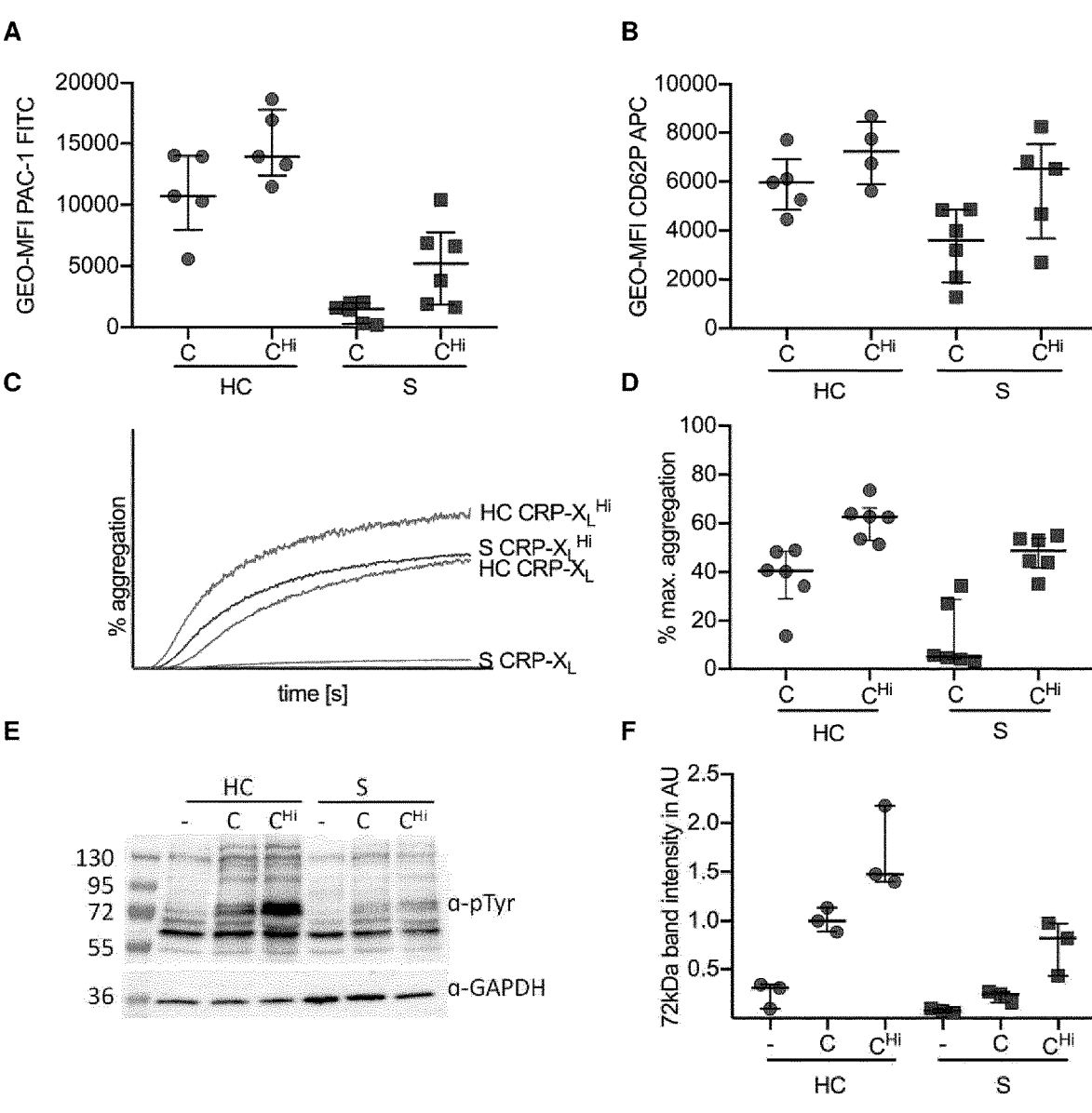

FIG. 6 shows that CRP-XL dose escalation leads to highly increased aggregation of sepsis platelets.

Platelet reactivity of healthy controls (HC) and patients with sepsis (S) is depicted upon stimulation with CRP-XL standard dose [0.1 µg/mL in aggregometry; 0.01 µg/mL in flow cytometry] and CRP-XL high dose (CRP-XLhi) [1 µg/mL] (A-B) Platelet activation due to integrin activation indicated through PAC-1 binding (A) or P-selectin exposure (B) was assessed in whole blood by flow cytometry. (C-D) Light transmission aggregometry was performed using washed platelets [500 000 1/µL]. Samples were measured for 5 minutes. Representative curves are shown in C. (D-E) Platelets were lysed after 5 minutes of CRP-XL stimulation or resting conditions. Staining was performed with phospho-tyrosine antibody 4g10. 72 kDa band intensity was set in relation to a housekeeping protein in arbitrary units (AU). Representative blots are shown in figure D (time point I). All graphs show median f IQR.

Figure 7:
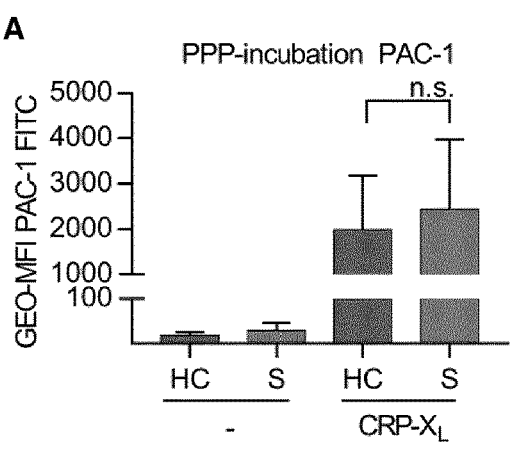
Figure 7:
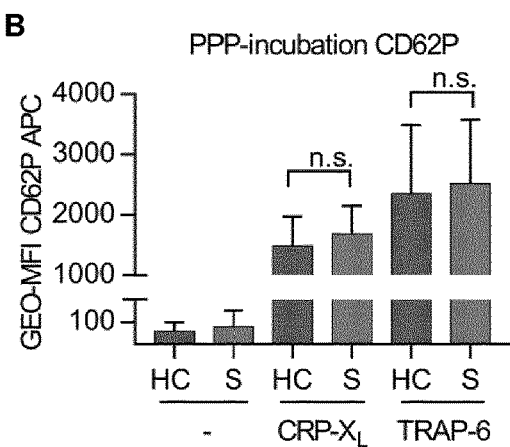
Figure 7:
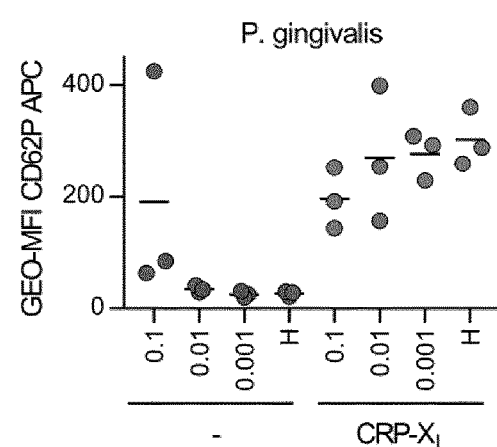
Figure 7:
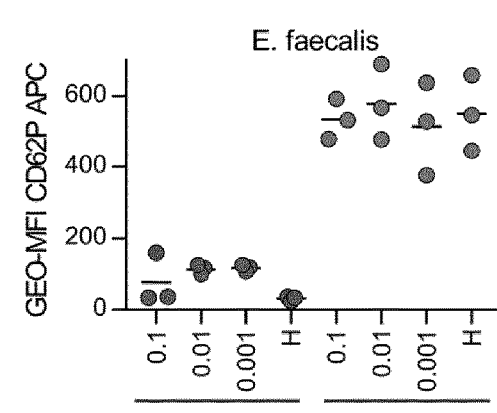
Figure 7:
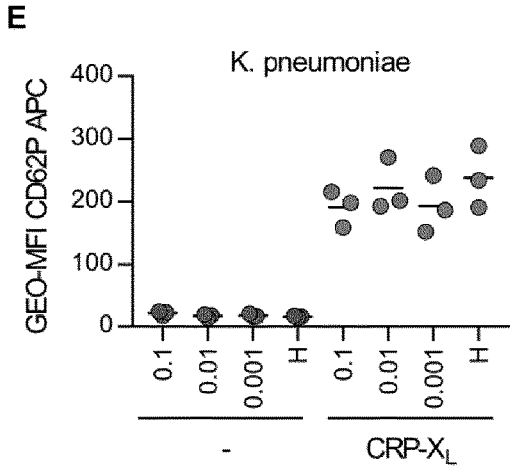
Figure 7:
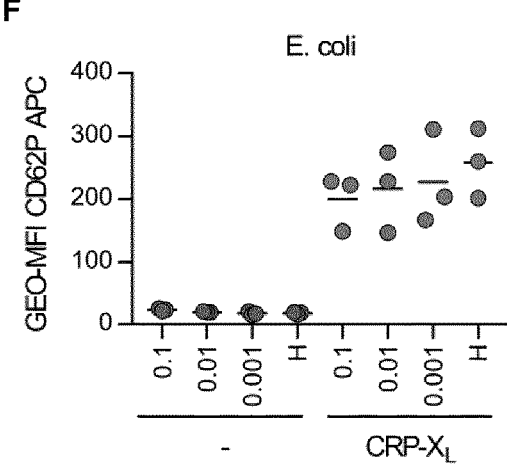

FIG. 7 shows that platelet hyporeactivity is not inducible through plasmatic factors and whole blood bacteria co-incubation.

Figure 8:
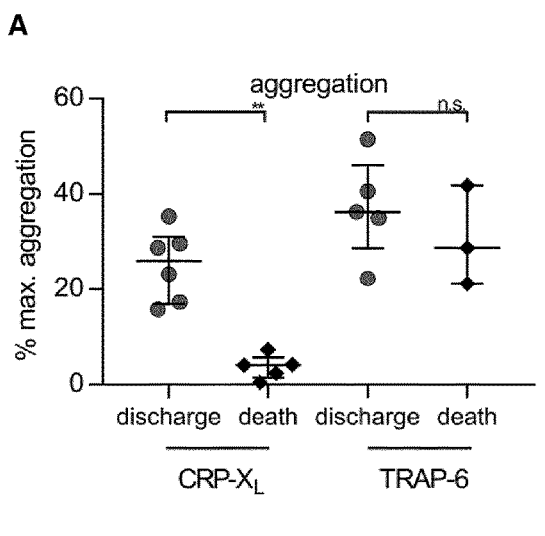
Figure 8:
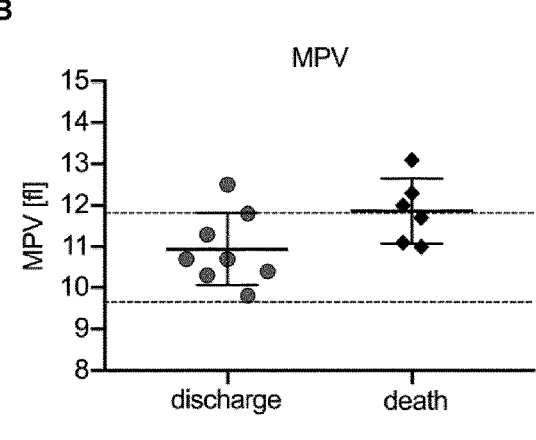
Figure 8:
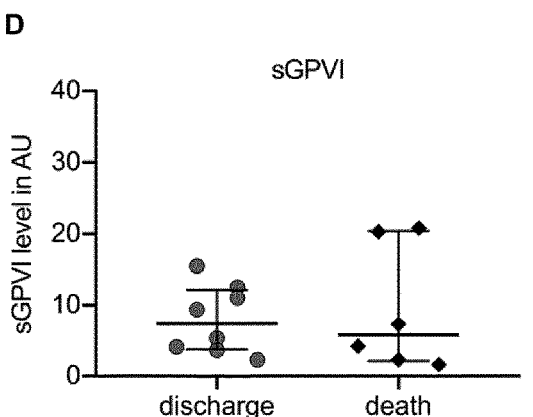
Figure 8:
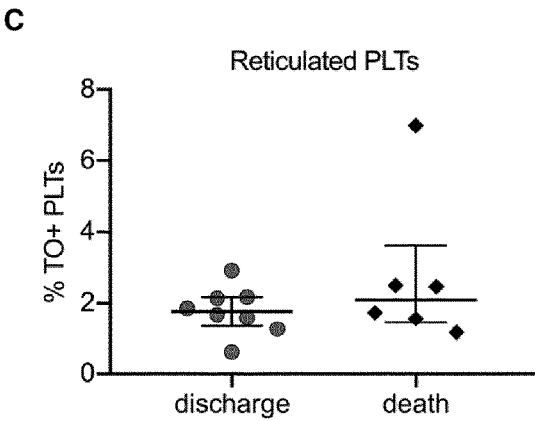
Figure 8:
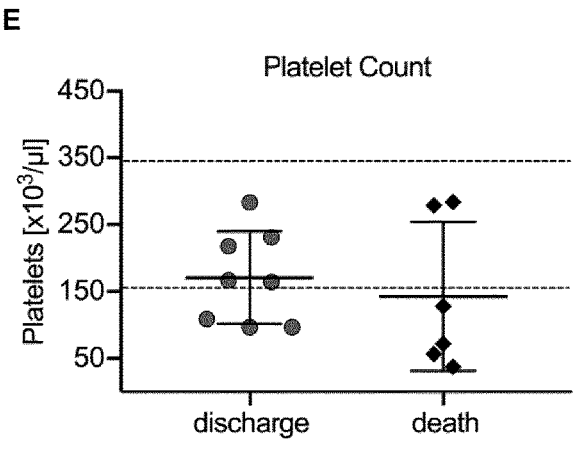
Figure 8:
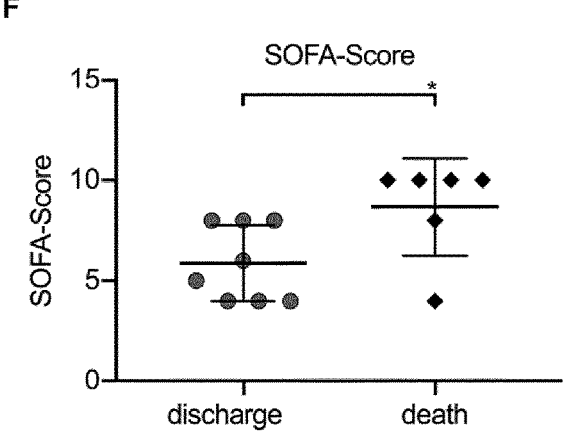

P-selectin exposure and integrin activation are shown under resting conditions (–) and upon activation with CRP-XL (C) [0.01 µg/mL] and TRAP-6 [5 µM] (T). (A, B) Platelets were incubated in PPP of sepsis patients (S) and healthy controls (HC) for 60 minutes. (n=8). (C-F) Whole blood of healthy donors was mixed with isolated bacterial strains adjusted to different OD's at 600 nM or modified Hepes-Tyrodes buffer (H). P-selectin expression was ana-lyzed on resting platelets (–) after 15 minutes. After incu-bation for 60 min platelets were stimulated with CRP-XL (C). (A-B) Data represents means t SD. (C-F) Data repre-sents means. (C-F) Differences were analyzed using Wil-coxon matched-pairs signed rank test. n.s. non-significant. All graphs show median±IQR FIG. 8 shows that platelet reactivity is highly correlating with outcome.

Figure 9:
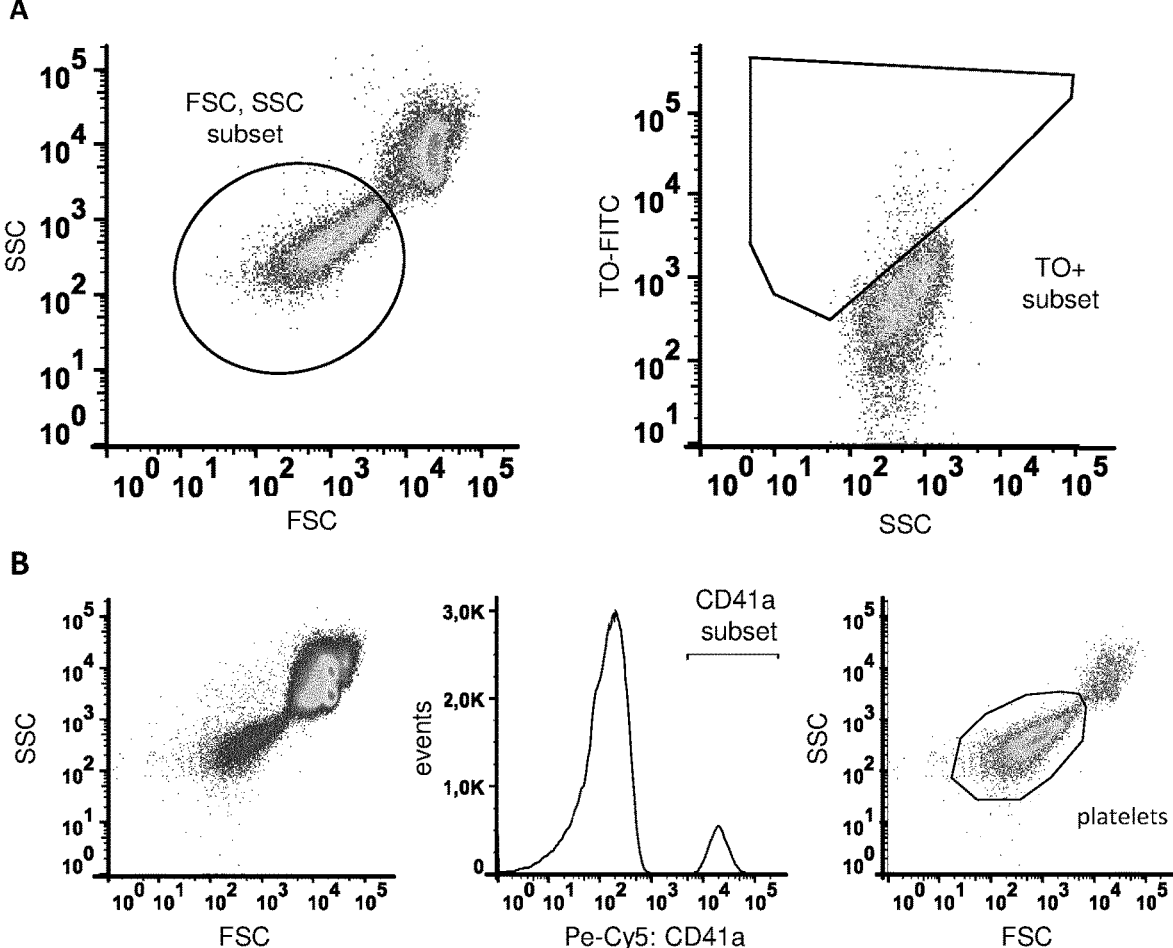

Last available values of each patient with sepsis are displayed (discharge/death). (A) Light transmission aggregometry was performed using washed platelets [500 000 1/µL]. Maximum aggregation is depicted upon stimulation with CRP-XL (C) [0.1 µg/mL] and TRAP-6 [5 µM](T). (B) mean platelet volume. (C) Reticulated platelets indicated as thiazole orange (TO) positive fraction were assessed by flow cytometry. (D) GPVI-ectodomain plasma-levels measured by ELISA. (E) Platelet count. (F) SOFA-Score. All graphs show median f IQR. Differences were analyzed using Kolm-ogorov-Smirnov test. n.s. non-significant, *p>0.05, **p>0.01, FIG. 9 shows gating strategies for FACS analysis. (A) Gating of reticulated platelets indicated as thiazol orange (TO) positive events (B) Gating of platelets in whole blood.

Figure 10:
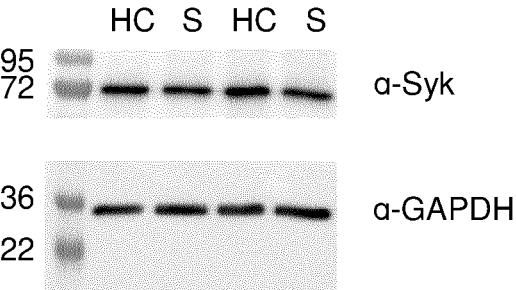

FIG. 10 shows that expression of Syk is unaltered in patients with sepsis. Western blot analysis of unstimulated platelet lysates of healthy controls (HC) and sepsis patients (S).

Figure 11:
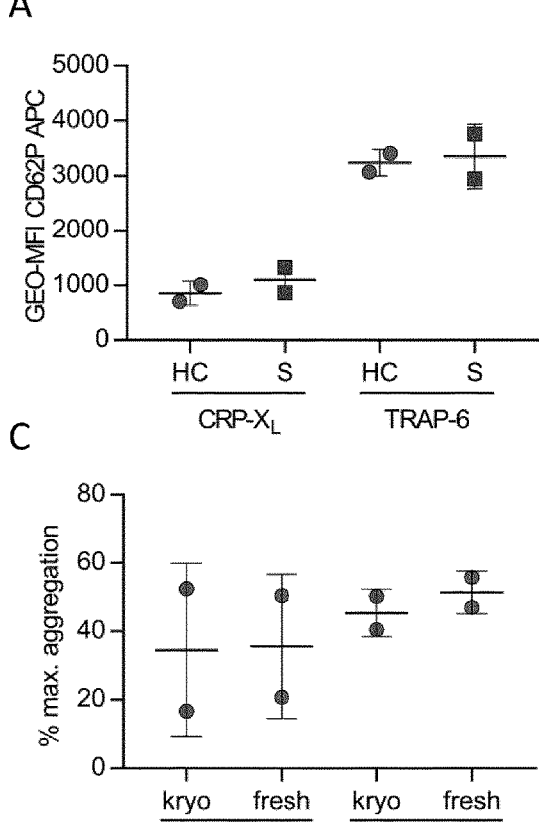
Figure 11:
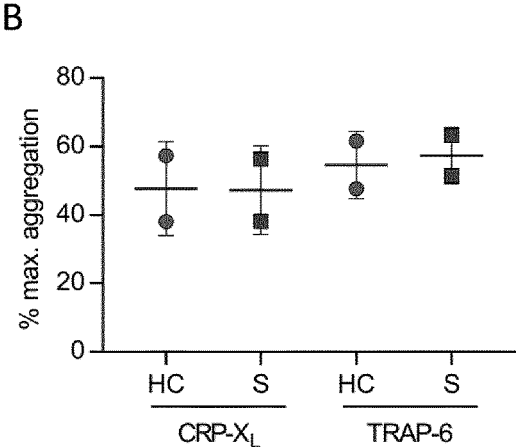

FIG. 11 shows that ABO incompatibility and plasma cryopreservation do not have an impact on platelet function in co-incubation experiments.

(A-B) Platelets were incubated in fresh plasma of sepsis patients (S) and corresponding healthy controls (HC) in the heating block for 60 minutes 37° C., 200 rpm. (B) Platelets were stimulated with CRP-XL (C) and TRAP-6 (T). P-selectin exposure was measured by Flow Cytometry (C) Platelets were incubated of either fresh or cryopreserved autologous plasma for 60 min-utes. Light-transmission aggregometry was subse-quently performed with washed platelets [500 000 1/µL] using CRP-XL (C) and TRAP-6.

Figure 12:
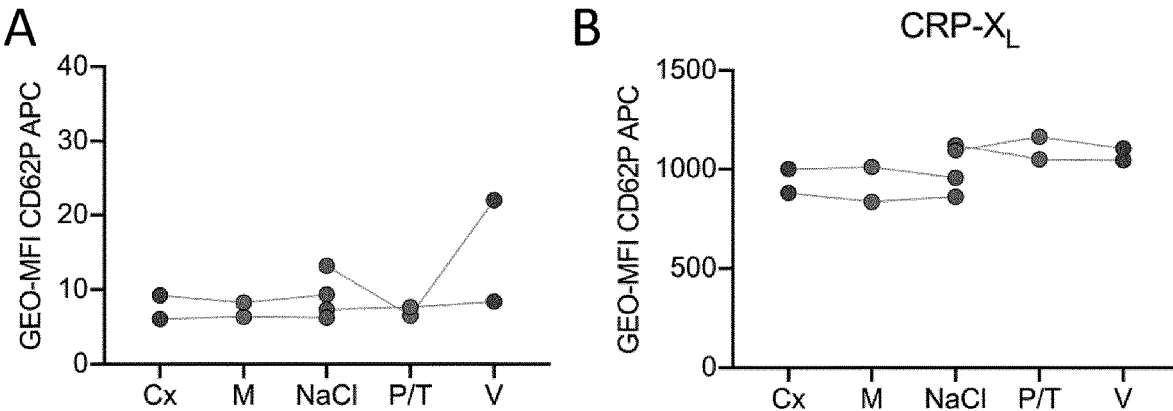

FIG. 12 shows that antibiotic drug therapy does not affect platelet reactivity. Antibiotics were added to whole blood of healthy donors. Incubation was performed for 2 h at 37° C. P-selectin exposure was determined subsequently by flow cytometry on resting (A) and CRP-XL [0.01 µg/mL] stimu-lated platelets (B). The following drugs were used: pipera-cillin/tazobactam [P/T=298 µg/mL; 4 µg/mL], vancomycin [V=60 µg/mL], metronidazole [M=25 µg/mL], ciprofloxacin [Cx=4.56 µg/mL].

Figure 13:
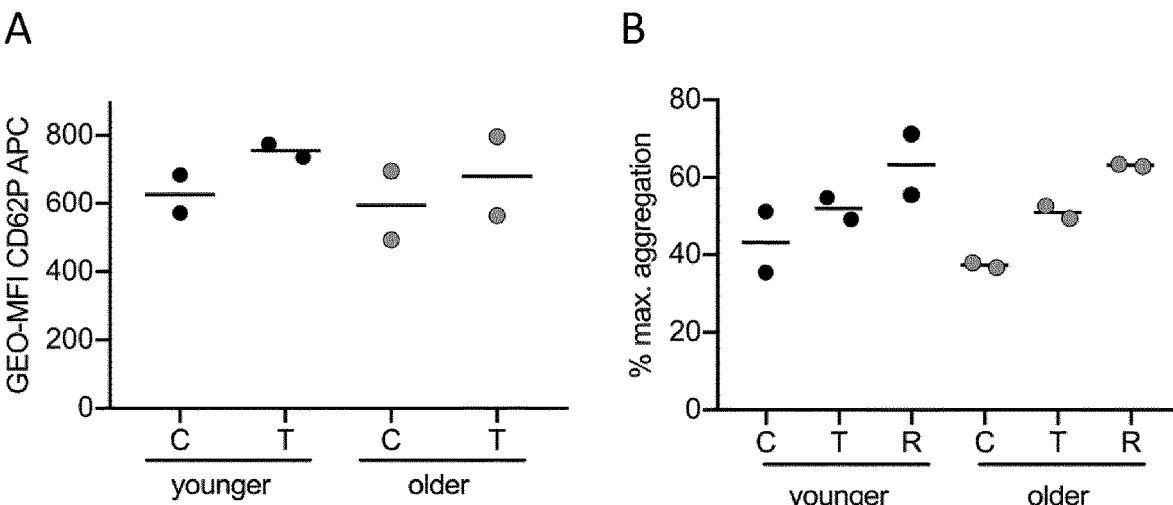

FIG. 13 shows that platelet function is independent of age. Platelet reactivity assays were performed with whole blood of a younger (mean age 23.5) and an older cohort (mean age 67). (A, B) P-selectin exposure was mea-sured upon stimulation with CRP-XL [0.01 µg/ml] (C) and TRAP-6 [5 µM] (T) in whole blood. Light trans-mission aggregometry was performed using washed platelets [500 000 1/µL]. Maximum aggregation is depicted upon stimulation with CRP-XL [0.1 µg/mL], rhodocytin [10 nM] (R) and TRAP-6 [10 µM]. Bars represent means.

Figure 14:
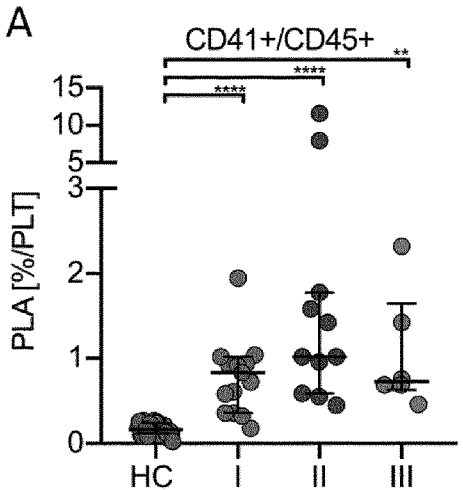
Figure 14:
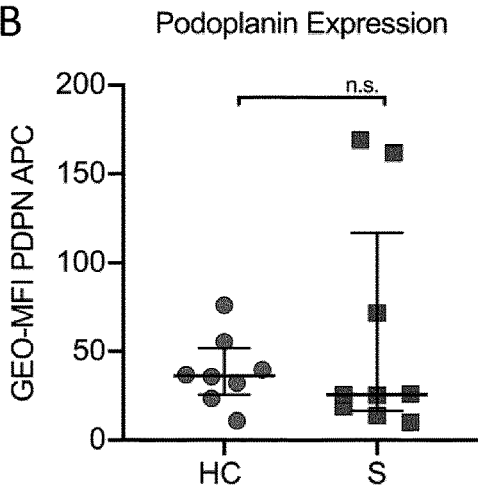

FIG. 14 shows that patients with sepsis have increased levels of platelet-leucocyte-aggregates.

(A) Platelet-leukocyte-aggregates (CD45+/CD41+) depicted in percent of total platelets. (B) Podoplanin-levels on CD45+ cells were measured in whole blood of sepsis patients (S) and healthy controls (HG) by flow cytometry. Graphs show median f IQR. Differences were analyzed using Kruskal-Wallis test (A), Kolmog-orov-Smirnov test (B). n.s. non-significant, *p>0.05, p>0.01, *p>0.001, ****p>0.0001.

Figure 15:
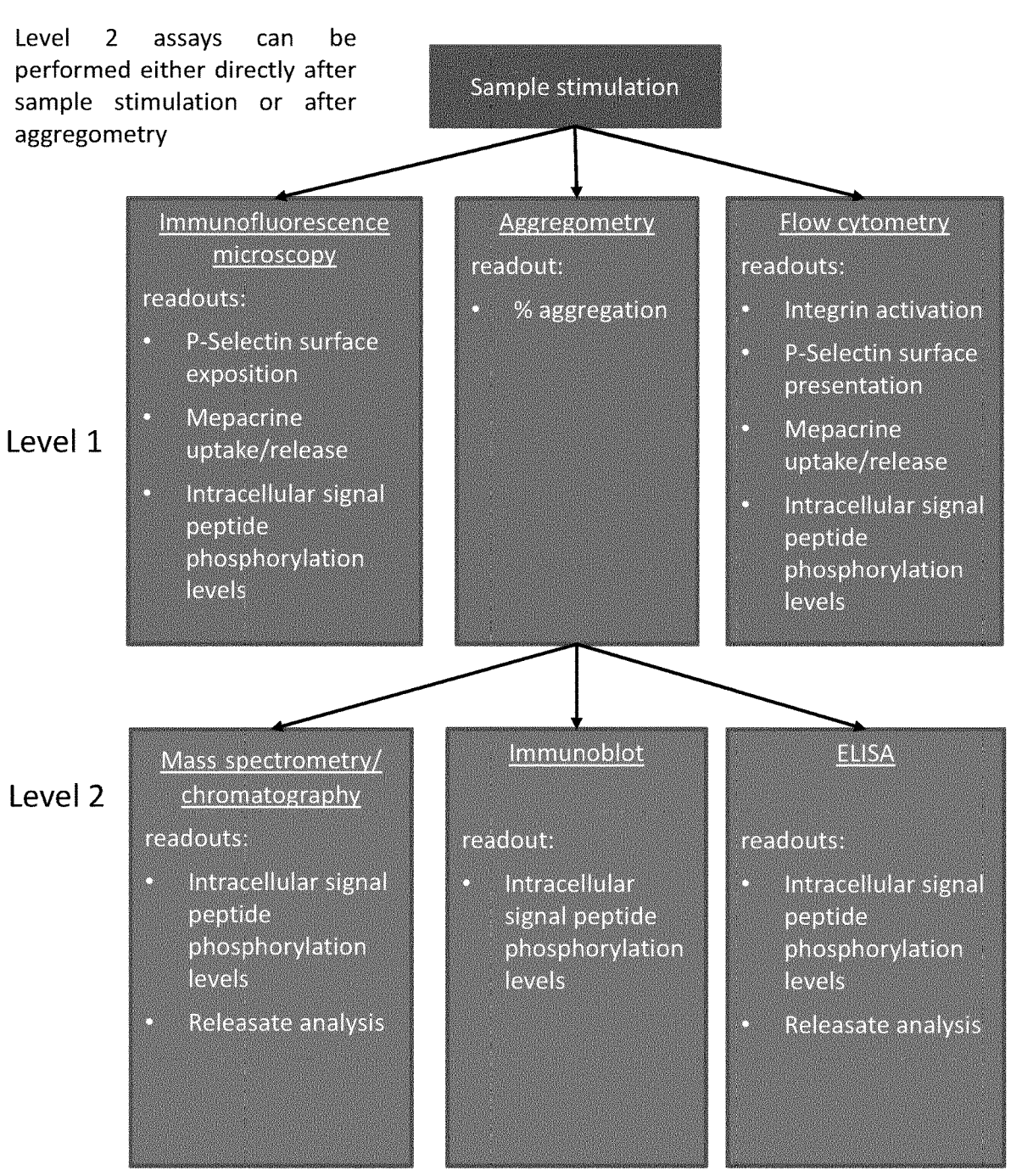

FIG. 15 shows a schematic flow chart of the various methodologies that are of use in a method of diagnosing a human sepsis. A platelet function level in a sample may be measured by different methods. Subsequent measurements may be performed using one sample, or different aliquots of one sample, for example firstly aggregometry and subse-quently any of mass spectrometry/chromatography, immu-noblot, and ELISA. The measurement methods and the readouts for measuring platelet function according to the present invention are represented in FIG. 15.

Figure 16:
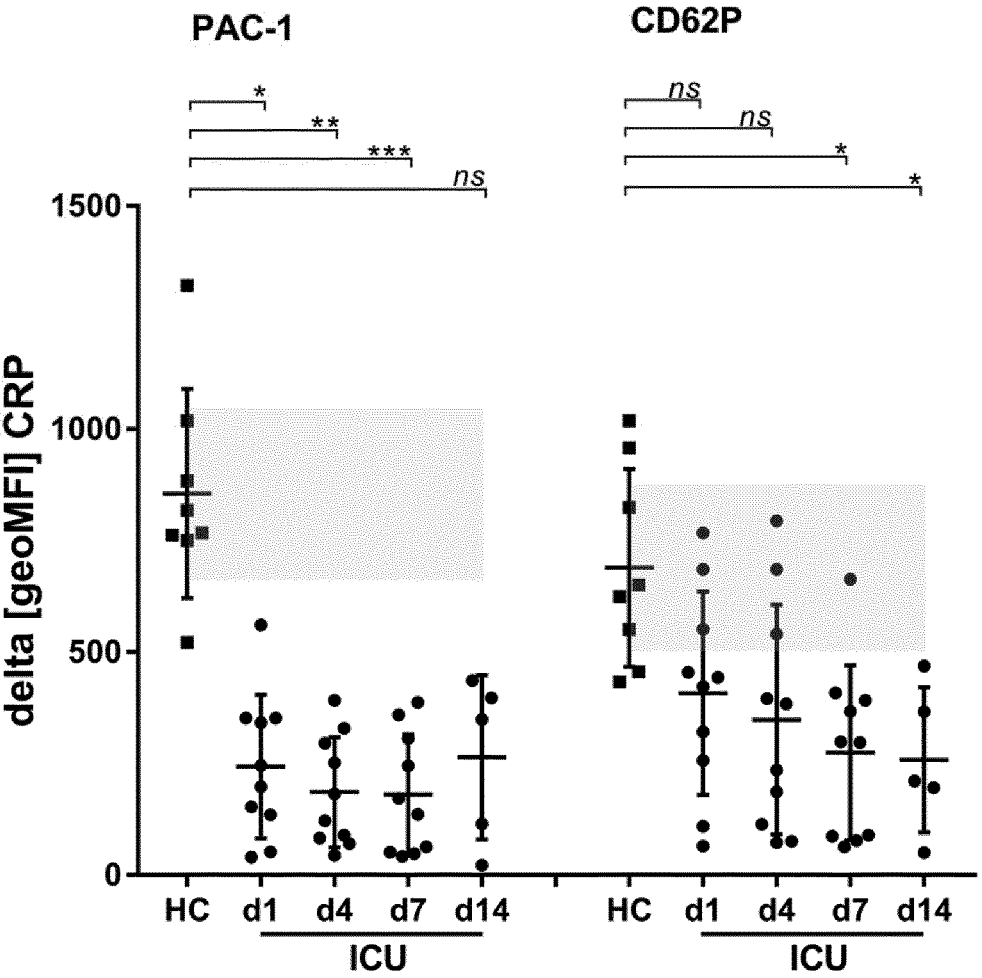

FIG. 16 shows the impaired response of Covid-19 patients to CRP-XL in a prospective longitudinal study. Analyses were performed flow cytometrically over a period of 14 days of stay at intensive care unit (ICU) with fibrinogen-receptor activation (PAC-1 antibody binding) and α-granule expo-sure (CD62P expression) as activation markers. Orange boxes indicate 95% confidence interval of the healthy con-trol (HC) cohort. geoMFI=geometric mean fluorescence intensity.

Figure 17:
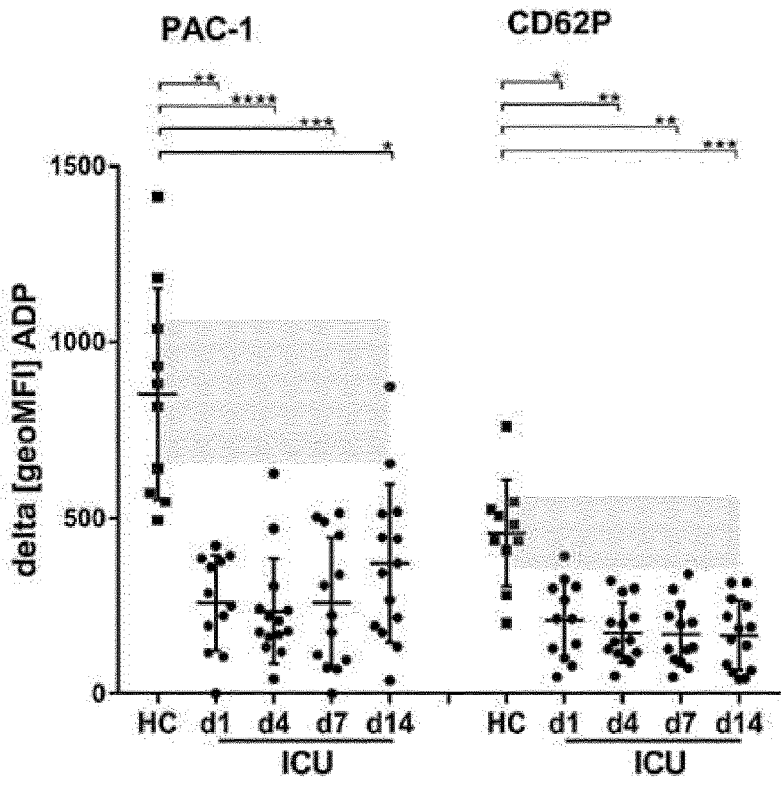
Figure 17:
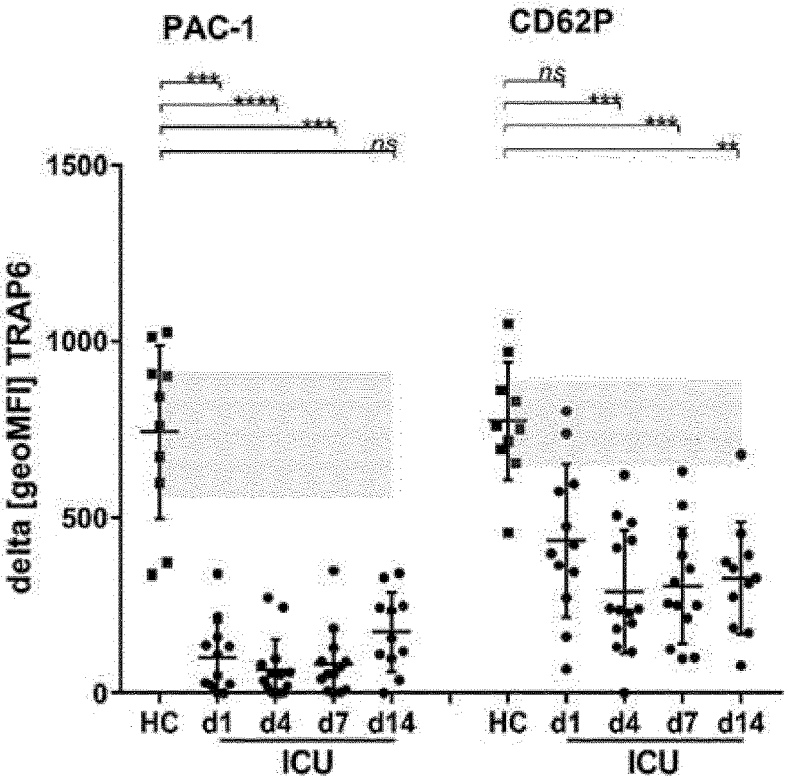

FIG. 17 shows the impaired response of Covid-19 patients to ADP and thrombin receptor agonist peptide (TRAP-6) optimized doses. Analyses were performed as stated for FIG. 16. Orange boxes indicate 95% confidence interval of the healthy control (HG) cohort. geoMFI=geometric mean fluo-rescence intensity. These findings demonstrate systemic platelet dysfunction in a homogenous critically ill cohort with defined pathogen depicting viral sepsis and increased SOFA score. This strongly indicates that platelet hyporeac-tivity correlates with the degree of disease, since Covid-19 patients show higher severity by means of heart-lung-ma-chine and ventilator or even extracorporeal membrane oxy-genation (ECMO) support.

In the following, reference is made to the examples, which are given to illustrate, not to limit the present inven-tion.

EXAMPLES

Example 1

Patient Recruitment and Blood Collection

Figure 1:
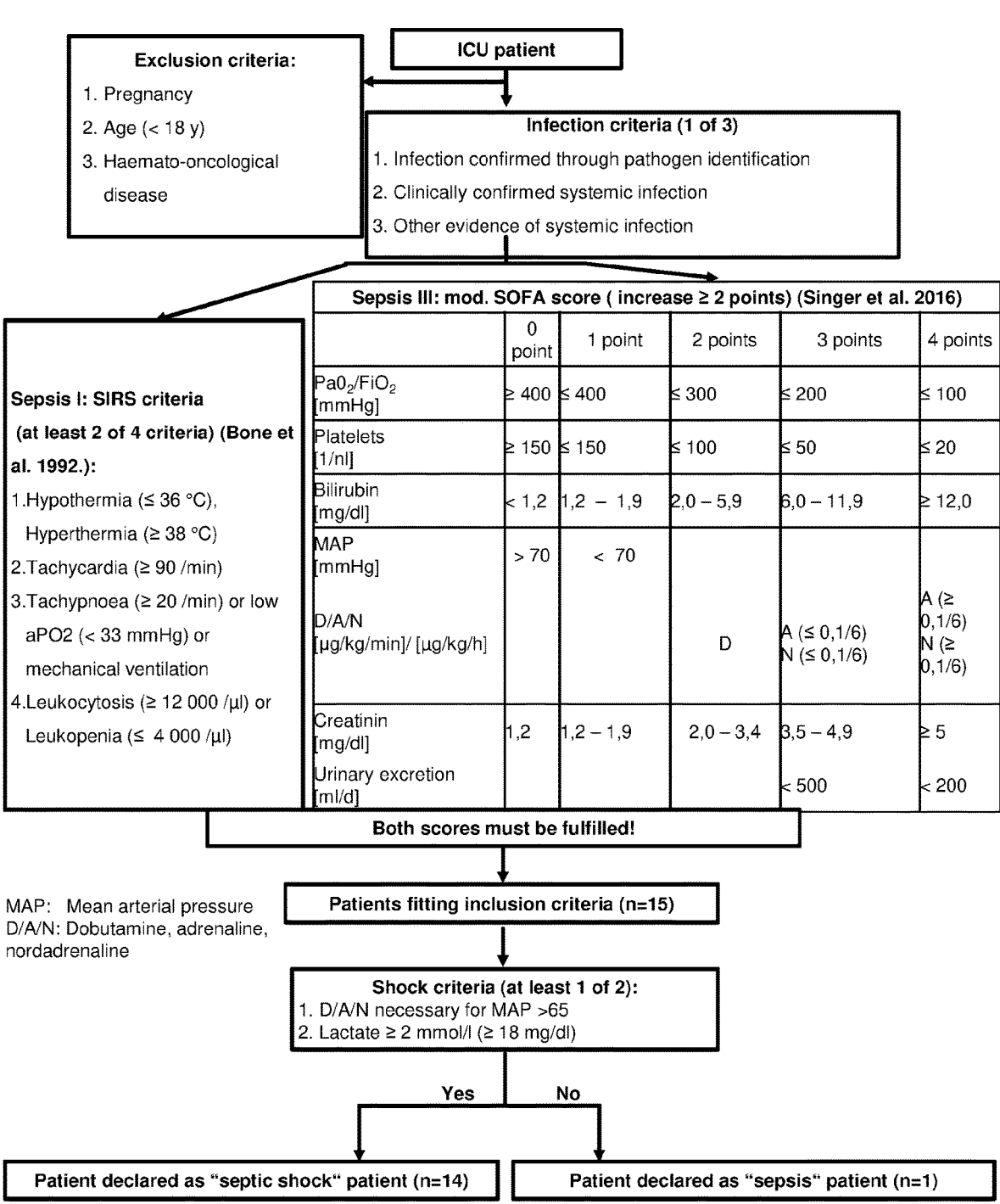
FIG. 1 shows a determination method for patient inclusion/exclusion.

The study was approved by the ethics committee of the University Hospital of Wuerzburg (reference number 102/ 17-sc) and conducted according to the declaration of Hel-sinki including its current amendments. Patients were recruited between September 2017 and Mai 2018. Venous blood was drawn from adult sepsis patients (age ≥18 y), that were administered at the intensive care unit of the university hospital Wuerzburg through routine-supply catheters in sodium-citrate (3.2%) monovettes. Informed consent was provided in written form by the patient, a family member or a legal guardian. Every patient was diagnosed with sepsis as well according to sepsis I as sepsis III criteria. Sepsis I criteria were fulfilled, if the patient was diagnosed with at least 2 of the following 4 SIRS criteria in addition to evidence of systemic infection: 1. hypothermia/hyperthermia 2. tachycardia 3. tachypnoea/pCO2 (<33 mmHg)/mechanical ventilation 4. leukocytosis/leukopenia. Sepsis III criteria were fulfilled if the patient had an increase in SOFA-Score of at least 2 points in addition to evidence of systemic infection. If fulfilling sepsis I and sepsis III criteria, patients were included with the diagnosis sepsis. If at least one of the following criteria was present additionally: 1. vasopressors are necessary for the maintenance of a mean arterial pressure >65 mmHG 2. serum-lactate ≥2 mmol/l, patients were diagnosed with septic shock (FIG. 1). Patients were excluded due to pregnancy and underlying haemato-oncological disease. Blood of healthy volunteers (age ≥18 y) was collected by venous puncture after informed consent was obtained in written form. It was ensured that healthy controls had not taken anti-platelet drugs for the last 10 days before blood sampling. The study was approved by the local ethic committee under.

Flow Cytometry

Whole blood was diluted 1:10 in modified HEPES-buffered Tyrode's solution (NaCl 137 mM, NaHCO$_3$12 mM, HEPES 5 mM, KCl 2.7 mM, MgCl2 1 mM, Na2HPO4 0.43 mM, glucose 0.1%, BSA 0.36%). Flow cytometry was conducted using a FACSCelesta™ flow cytometer (Becton Dickinson, Franklin Lakes, NJ, USA). Prior to reactivity measurement, platelets were incubated with respective agonists at indicated concentrations for five minutes. Staining of reticulated platelets was performed using thiazole orange (Sigma Aldrich, St. Louis, MO, USA) for 60 min at room temperature protected from light. After antibody addition samples rested for 15 min in the dark until the reaction was stopped with addition of 1.5 mL FACS-Flow sample buffer (Becton Dickinson).

Plasma Incubation

Experiments were performed using cryopreserved platelet poor plasma (PPP) of sepsis patients and the corresponding controls. Plasma was slowly thawed on ice and centrifuged at 2000 g for 10 min. Platelets were washed and resuspended in PPP. Incubation was performed for 60 min at 37° C. Afterwards, platelet stimulation was performed.

Platelet Washing and Aggregometry

After centrifugation of whole blood at 152 g for 20 min, platelet rich plasma (PRP) was separated and incubated in acetylsalicylic acid (ASS) for 30 min (final concentration 2 µM). Prostaglandine E1 (1 µM) and apyrase (2 U/mL) were added and platelets were washed with modified HEPES-buffered Tyrode's solution once (1000 g, 10 min). PPP was cryopreserved for further investigation. Afterwards platelet count was adjusted to 500 000 1/µL through resuspension in re-calcified Hepes buffered Tyrode's solution (CaCl$_2$) 2 mM). Light transmission aggregometry was performed using an APACT 4S (LABiTec, Ahrensburg, Germany) aggregometer at 37° C. stirring conditions. Maximum aggregation was assessed in percent in relation to re-calcified Hepes buffered Tyrode's solution as blank. For further molecular analysis platelets were lysed through addition of ice-cold 2x lysis buffer (NaCl150 mM, HEPES 15 mM, EGTA10 mM, Triton X-100 2%, Na3VO4 2 mM, PMSF 1 mM, Aprotinin A 1 mM, Leupeptin 1 mM, Pepstatin 1 mM).

Immunoblotting

Platelet lysates were treated with 4×SDS sample buffer and boiled at 95° C. After separation through gel electrophoresis, protein was blotted on nitrocellulose-membranes followed by blocking, washing and incubation with different antibodies. Western Blots were imaged using an HRP-substrate solution and an Amersham Imager 600 (GE Healthcare, Little Chalfont, GB).

ELISA

ELISA was performed as described previously. GPVI standard curve was obtained by using the supernatant of carbonyl cyanide m-chlorphenylhydrazone (CCCP) [100 mM] stimulated platelet suspension in serial dilution from 1:1 to 1:64. TPO and IL-6 plasma levels were determined using Quantikine® ELISA kits (R&D, Minneapolis, MN, USA) according to manufacturer's manual.

Bacteria

Bacterial strains were characterized and isolated during microbiological routine diagnostics and stored at −20° C. in glycerol stocks. Bacteria were expanded overnight at 37° C. on blood agar, MacConkey agar or Brain Heart Infusion (BHI) media while shaking. *Porphyromonas gingivalis* was cultured under anaerobic conditions on Schaedler agar for 72 h at 37° C. Isolates were centrifuged, washed and subsequently resuspended in HEPES-buffered Tyrode's solution. OD600 nm was adjusted to 1, 0.1 and 0.01. One part Bacteria-suspension was mixed with nine parts of whole blood of healthy donors (1:10). Incubation was performed for 60 min at 37° C. in the heating block with subsequent platelet stimulation.

Statistical Analysis

Statistical analysis was performed using graph-pad prism version 8.0.0 (GraphPad Software Inc., La Jolla, CA, USA). Results are presented as median±interquartile range or mean±standard deviation. Significance was considered for $p<0.05$.

Example 2

All methods were carried out as described in the previous example.

15 patients diagnosed with sepsis according to sepsis I and sepsis III criteria were recruited between September 2017 and May 2018 from two intensive care units (ICU) of the University Hospital Wurzburg (for the detailed determination method see FIG. 1) and followed up during disease progression and at day of discharge from the ICU.

The median age was 70 years with a range of 19 to 84 years. The infect focus, the identified pathogens as well as the applied therapies were diverse (Table 1, Table 2). As control group 19 healthy individuals (median age 32 years; range 22 to 61) were included that had not taken platelet function-relevant medication (COX inhibitors or thienopyridines) for 10 days prior to blood withdrawal.

TABLE 1

| Patient characteristics. | |
| --- | --- |
| Patient characteristics | Sepsis n = 15 |
| Mortality | 6/15 |
| DIC (DIC-Score ≥5) | 4/15 |
| Isolated pathogen | |
| Gram− | 8/15 |
| Gram+ | 3/15 |

TABLE 1-continued

Patient characteristics.

| Patient characteristics | Sepsis n = 15 |
|---|---|
| Gram+ and Gram– | 3/15 |
| Unknown | 1/15 |
| Infection site | |
| Respiratory | 9/15 |
| Urinary | 3/15 |
| Other | 3/15 |
| Comorbidity | |
| CHI | 2/15 |
| COPD | 3/15 |
| Diabetes mellitus | 5/15 |
| Chronic kidney disease | 3/15 |
| Devices | |
| CVVH | 7/15 |

TABLE 2

Identified pathogens.

| ID | Observed Bacteria (material) | Antibiosis at times of blood sampling |
|---|---|---|
| 21 | *Enterococcus faecium* (5, 9) | P/T, X |
| 22 | *Escherichia coli* (2) | M, A/S, Cx, V |
| 23 | *Klebsiella pneumoniae* (1, 2) * | Mp, V |
| 24 | *Staphylococcus haemolyticus** (5) | P/T, Cx, Mp, V, Cm, Mx, Cz |
| 25 | / | P/T, V, M |
| 26 | *Pasteurella multocida, Proteus mirabilis* (3) | P/T, Cx, V |
| 27 | *Enterobacter hormachei* (8), *Enterococcus faecium* (8), *Enterobacter cloacae* (4, 5) | P/T, Lx, Lz |
| 28 | *Escherichia coli** (1) | P/T, A/S, Cx |
| 29 | *Enterococcus faecium* (1) *, *Escherichia Coli* (8) | P/T, Cx |
| 30 | *Pseudomonas aeruginosa* (1, 6) | P/T, Cx, V |
| 31 | *Escherichia coli* (2) | P/T, M |
| 32 | *Escherichia coli* (7), *Klebsiella pneumoniae* (7), *Enterococcus faecium* (7) | P/T, Ip |
| 33 | *Klebsiella oxytoca* (2) | V, Mp, Cx, E |
| 34 | *Escherichia coli* (1, 8) | P/T, Cx |
| 35 | *Enterococcus faecium* (1) | M, Mp |

\* bacteria were isolated and used for platelet-bacteria co-incubation assays.
P/T: Piperacilin/Tazobactam°
X: Rifaximin
A/S: Ampicilin/Sulbactam
M: Metronidazole°
Cx: Ciprofloxacin°
Lx: Levofloxacin
Ip: Imipinem
E: Erythromycin
Cm: Clarithromycin
Mx: Moxifloxacin
Lz: Linezolid
Mp: Meropenem
V: Vancomycin°
Cz: Ceftazidim
°antibiotics were tested in platelet-antibiotic co-incubation assays.
1: Blood culture
2: Tracheal secrete
3: Brochoalveolarlavage
4: Pleural-punctate
5: Catheter tip
6:Wound swab
7: Abdominal cave swab
8: Urin
9: Ascites

Circulating Platelets in Sepsis are not Pre-Activated.

Thrombocytopenia is a predominant finding in sepsis. According to the SOFA-criteria, infection together with platelet counts less than 100/nL is sufficient for diagnosing sepsis and indicates a poor prognosis. On ICU admission, median platelet count in the cohort was 167/nL (IQR 122.5; 231.5). Eight patients had a normal platelet count, five patients were thrombocytopenic (less than 150/nL) and two patients had counts above 350/nL. Platelet counts decreased in 6/10 patients with initially regular or increased platelet count below the lower reference value during the first week on ICU, on average after 1.6 days. Two patients did not develop thrombocytopenia during the course of disease. Until the day of discharge, platelet counts normalized in every patient (FIG. 2A). In order to determine whether sepsis had an impact on platelet production, the fraction of thiazole orange (TO)-positive platelets was measured which serves as a marker for newly formed platelets due to residual RNA derived from megakaryocytes. A significant gain of TO-positive platelets was observed during the first five days at ICU at time point II (FIG. 2B) Also thrombopoietin (TPO) plasma levels increased significantly, suggesting unaltered feed-back signaling for platelet biogenesis during the course of sepsis (FIG. 2C). Finally, mean platelet volume (MPV) increased significantly until time point II, also indicating an increasing fraction of newly formed platelets that are typically larger in volume (FIG. 2D).

Expression levels of the main platelet surface receptors for von Willebrand factor (GPIb/IX) and fibrinogen (GPIIb/IIIa), as well as integrin β1 remained unchanged (FIG. 2E). Considering ectopic platelet activation to explain increased platelet consumption, pre-activation was tested by flow cytometry. For this, integrin αIIbβ3 activation (PAC-1 antibody binding) and α-granule release (P-selectin/CD62P surface exposition) were measured. Expression of these activation markers, however, was not significantly altered in resting platelets (FIG. 2F-I). Pre-activation was also not detected in patients diagnosed with disseminated intravasal coagulation (DIC), according to a DIC-score of 5 or more (data not shown) although these patients usually suffer from severe (micro-)thrombotic events together with platelet consumption.

ADP stimulation platelet reactivity was also highly impaired (FIG. 3G-H). Interestingly platelet hyporeactivity was observed days before decreasing platelet counts suggesting circulation and subsequent clearance of dysfunctional platelets during disease progression. After stimulation with every used agonist platelet degranulation indicated by CD62P exposure was less affected compared to integrin αIIbβ3 activation.

Platelet aggregation was measured by light transmission aggregometry (LTA), in case patient-derived material was sufficient. For all those corresponding patients LTA was performed with CRP-XL as the major agonist and found a markedly reduced aggregation in all sepsis patients compared to healthy controls. At time point III (discharge from ICU), the present inventors found that the maximal platelet

TABLE 3

| | | | |
|---|---|---|---|
| Characterization of blood samples. | | | |
| Laboratory values, median (IQR) | (I) Admission day (n = 15) | (II) Day 5-7 at ICU (n = 11) | (III) ICU discharge (n = 7) |
| WBC [5 000-12 000 1/μL] | 19 150 (11 050-23 725) | 11 300 (8350-14 375) | 7 500 (7 000-9525) |
| RBC [4-6 * 10⁶ 1/μL] | 3.31 (3.09-3.51) | 2.47 (2.39-2.69) | 2.87 (2.32-3.11) |
| Hb [14-18 g/dL] | 10.2 (9.7-11.0) | 8.0 (7.45-8.35) | 8.6 (7.6-9.4) |
| Hk [42-50%] | 29.9 (28.8-33.1) | 23.8 (21.8-25.4) | 25.7 (22.9-28.6) |
| MCV [82-94 fL] | 92.6 (89.8-96.6) | 91.9 (90.6-96.2) | 92.9 (91.0-95.2) |
| MCH [27-33 pg] | 30.7 (29.8-32.5) | 31.7 (30.0-33.5) | 30.2 (30.0-31-6) |
| MCHC [32-36 g/dL] | 33-3 (33.1-34.2) | 33.8 (33.3-34.0) | 33.2 (32.7-33.3) |
| Creatinin [0-1.17 mg/dL] | 1.94 (1.40-2.86) | 1.69 (1.13-2.45) | 3.54 (1.72-5.33) |
| Bilirubin [0.1-1.2 mg/dL] | 1.7 (0.9-5.0) | 2.3 (1.3-5.1) | 1.7 (1.2-3.8) |
| Urea [10-50 mg/dL] | 84.2 (63.1-130.6) | 77.1 (36.75-128.2) | 81.25 (36.8-102.2) |
| C-reactive protein [0-0.5 mg/dL] | 25.8 (19.9-33.0) | 12.6 (11.1-16.8) | 5.5 (3.8-6.5) |
| PCT [0-0.5 ng/dL] | 21.4 (6.1-48.5) | 14.3 (8.5-28.0) | / |
| Severity Scores | | | |
| SOFA | 9 (8-11) | 9 (7.5-10) | 5 (4-7.5) |

WBC: white blood cells
RBC: red blood cells
Hb: hemoglobin
Hk: hematocrit
MVC: mean corpuscular volume
MCH: mean corpuscular hemoglobin
MCHC: mean corpuscular hemoglobin concentration
PCT: procalcitonin Platelets in Sepsis are Hyporeactive.

Many sepsis patients from the cohort were thrombocytopenic or anemic. As several point-of-care tools that have been developed for basic on-site evaluation of platelet function and bleeding risk are limited due to pre-analytic requirements like minimal platelet count or hematocrit, a comprehensive platelet function analysis comprising light transmission aggregometry and flow cytometry was performed.

The following compounds were used as agonists: ADP to stimulate the purinergic receptors P2Y12 and P2Y1, a synthetic crosslinked collagen-related peptide (CRP-XL), or the snake-venom convulxin to stimulate the collagen receptor GPVI on platelets.

In 14 of 15 patients of the cohort, significantly blunted platelet activation was found in response to stimulation with 0.01 μg/mL CRP-XL at the day of ICU admission. This is evident by both, abolished PAC-1 binding as well as lack of CD62P exposure (FIG. 3A-D). When using the snake venom convulxin (i.e. 0.01 μg/mL) as GPVI agonist impaired platelet activation was still evident, albeit to a lesser extent compared to CRP-XL (FIG. 3E-F). This can be explained by the multi-valent binding properties of convulxin, leading to increased GPVI clustering compared to CRP-XL. Upon aggregation rate in response to 0.1 μg/ml CRP-XL revealed an tendential recovery, though not significant (FIG. 3I-J).

This abolished aggregation was found in 5/8 patients at time point I when 10 nM rhodocytin was used as a CLEC-2 agonist, while three patients showed completely normal aggregation upon rhodocytin stimulation. Maximum aggregation upon rhodocytin stimulation had completely recovered at day of discharge (time point III) (FIG. 3K-L). Upon stimulation with 10 μM of the selective PAR-1 receptor agonist TRAP-6 sepsis platelets showed an increased aggregation potential of minimum 21.2% at day of ICU admission (mean 34.2%) in every studied patient, indicating a remaining aggregation potential of platelets under septic conditions (FIG. 3M-N).

Platelets in Sepsis Show Increased GPVI Ectodomain Shedding.

To exclude the possibility that deficient platelet function is caused by altered receptor expression, GPVI and CLEC-2 surface levels were analyzed by flow cytometry. While CLEC-2 surface presentation on platelets was unaltered, the present inventors found that GPVI expression was partly reduced compared to healthy controls (FIG. 4A-B). Thus, it was assessed whether it was possible to find evidence for one of the two known mechanisms for GPVI removal from the platelet surface (ectodomain-shedding or receptor internalization) (Dutting 2012 Trends Pharmacol Science). In platelet lysates, a slightly reduced expression of GPVI was detected by immunoblot analysis (FIG. 4C). GPVI expression was further decreased when platelets were first activated with CRP-XL. This suggests that ectodomain-shedding of the GPVI receptor is responsible for this finding rather than receptor internalization. In line with this, soluble GPVI ectodomain levels increased in plasma and were elevated at day 5-7 at the ICU (time point II) compared to normal plasma (FIG. 4D).

Platelets in Sepsis Show Impaired (Hem-)ITAM Signaling.

GPVI and CLEC-2 are (hem)-ITAM immunoreceptors, associated with the FcRy chain, which transduces the stimulatory signal via Src family kinases and Syk to the LAT signalosome and PLCy2, resulting in calcium influx and platelet activation. Both receptors were also shown to be key regulators during immuno-inflammatory processes. Therefore, the GPVI/CLEC-2 signaling cascade in patients with sepsis was analyzed in more detail.

Analysis of global tyrosine phosphorylation by immunoblot using an anti-phosphotyrosine antibody (clone 4G10) revealed no elevated basal phosphorylation levels in resting platelets. Additional pTyr bands were readily inducible in healthy donors when platelets were stimulated with 0.1 µg/mL CRP-XL or 10 nM rhodocytin. In contrast, tyrosine phosphorylation was not inducible in platelets of sepsis patients. This is particularly demonstrated for the 72 kDa band which is known to reflect the phosphorylated Syk kinase. With clinical recovery, platelet aggregation ameliorated (time point III) and the inducible tyrosine phosphorylation pattern reached almost normal levels (FIG. 5A-C). To further identify the underlying relevant signaling molecules, phospho-epitope-specific antibodies directed against tyrosine residues 525/526 of pSyk or tyrosine residue 191 of p-Lat were used and it was confirmed that the ITAM-signaling cascade downstream of GPVI is markedly affected in patients (FIG. 5D-F).

Immunoreceptor tyrosine inhibitory motif (ITIM) containing receptors are major negative regulators of ITAM-receptor signaling and play an important role for negative feedback signaling after platelet stimulation. The main ITIM receptors expressed on platelets are PECAM-1, G6b-B, TLT-1, CEACAM-1, and -2. ITAM-mediated platelet activation have been shown to lead to subsequent phosphorylation of the SH2-domain containing protein tyrosine phosphatases SHP-1 and SHP-2. One possible mechanism for the impaired GPVI signaling could be a partial or constitutive ectopic activation of those two phosphatases expressed in platelets. The present inventors thus analyzed protein lysates of resting, CRP-XL- and rhodocytin-stimulated platelets for the presence of activation-dependent phospho-epitopes by immunoblotting. The present inventors did not detect any increased phosphorylation levels of SHP-1 or SHP-2 under resting conditions in platelets from patients compared to healthy controls. The present inventors also could not detect the physiologic increase in SHP-1 and SHP-2 phosphorylation upon CRP-XL or rhodocytin stimulation, which is typically induced to limit the ITAM signaling pathways (FIG. 5G-J). This observation indicates that increased SHP-1 and SHP-2 activity is unlikely to be causative for the activation defect in sepsis patients and suggests that the sepsis-mediated defect is located upstream in the ITAM-receptor cascades due to the dysfunctional feedback mechanism.

CRP-XL Dose Escalation Increased Activation and Aggregation of Platelets in Sepsis.

Following up to the results from flow cytometry, aggregometry, and immunoblotting, the present inventors asked whether the signaling defect could be overcome by dose escalation, which might also trigger GPVI receptor cross-linking. Indeed, when CRP-XL was increased 10 fold in aggregometry (and 100 fold in flow cytometry), the response was normalized as normal CD62P exposure and integrin αIIb/β3 activation was found. Moreover, maximum aggregation increased up to reference levels (FIG. 6A-D), concomitantly with the induced tyrosine phosphorylation levels, detected by immunoblotting (FIG. 6E-F). Taken together, the data strongly imply that during sepsis signaling cascades are preserved but rather downregulated than completely impaired in circulating platelets.

Platelet Hyporeactivity is not Inducible Through Plasmatic Factors and Through Whole Blood Bacteria Co-Incubation.

The hitherto assessed results do not allow to differentiate whether hyporeactive platelets are produced during megakaryopoesis in septic patients, or whether platelet dysfunction is induced in circulating platelets. The present inventors thus incubated platelets either in plasma of septic patients or healthy controls prior to performing stimulation experiments. Incubation of resting platelets from healthy donors in plasma of sepsis patients did not result in platelet activation, as shown by a resting CD62P expression level or absent PAC-1 binding and caused no altered response to CRP-XL or TRAP-6 (FIG. 7A-B and FIG. 11A-B). The present inventors found no difference in platelet activation independent of whether freshly isolated platelet poor plasma (PPP) was used or cryopreserved PPP, as confirmed by flow cytometry or aggregometry. The data imply that platelet hyporeactivity is not primarily induced by plasmatic factors.

In 14 of 15 patients, at least one bacterial strain could be identified, underlying the sepsis-connected infection (Table 2). As several strains can directly or indirectly affect platelet function, the present inventors next analyzed whether the GPVI signaling defect is affected by the isolated bacteria. The present inventors expanded and purified one Gram-positive (Enterococcus faecalis, ID-S29) and two Gram-negative strains (Escherichia coli ID-S28 and Klebsiella pneumoniae ID-S23), which were kept under either solid or planktonic growth conditions. Platelets were isolated from three distinct healthy controls and co-incubated with the bacteria in a serial dilution of 0.1 to 0.001 OD600 nm. As a positive control, a distinct Porphyromonas gingivialis strain was used which induces platelet aggregation. Upon co-incubation with the highest concentration (OD600 nm=0.1) of P. gingivalis, platelets became activated indicated by CD62P surface presentation. Surprisingly, besides P. gingivalis, only incubation with E. faecalis led to discrete activation of resting platelets (FIG. 7C-F). Incubation with K. pneumonia or E. coli did not induce CD62P exposure. After co-incubation with the bacteria, platelets of all three healthy controls demonstrated an unaltered response to CRP-XL stimulation. Taken together, the results imply that the defective ITAM-signaling is not induced by platelet-bacterial interactions.

As all sepsis patients received antibiotic therapy, the present inventors next evaluated whether antimicrobial drugs could reduce GPVI/CLEC-2 reactivity. The present inventors selected the broadly used antibiotics piperacillin/tazobactam, ciprofloxacin, metronidazole and vancomycin which differ in mode of action and do not require first-pass activation (Table 2) for incubation with whole blood of healthy donors at therapeutic peak plasma levels. As shown in FIG. 12, none of these drugs had an impact on GPVI-mediated platelet reactivity, making a cross-reaction of antibiotic drugs unlikely.

GPVI Deficiency is Associated with Critical Illness.

The question arised whether any intrinsic disease-related alteration is associated with platelet defectiveness. Neither elevated inflammatory markers (CRP, leukocytes) nor obvious clinical laboratory values or scores (creatinine, urea, bilirubin) correlated with decreasing or improving platelet reactivity. Interestingly, the present inventors observed that platelet aggregation recovered in those patients discharged from ICU, compared to those patients that deceased after the last measurement. The present inventors compared clinical and diagnostic parameters at the last documented visit with corresponding samples (death vs. discharge; see also Table 4). Aggregation upon CRP-XL stimulation recovered in discharged patients, compared to the patients who died (median time of death after the last measurement: 6 d; Range 3-12 d) (FIG. 8A). In contrast, the present inventors found no differences for TRAP-6- or rhodocytin-triggered reactivity (FIG. 8A). Furthermore, other platelet-related parameters like overall count, MPV, fraction of TO-positive platelets or the plasma level of sGPVI ectodomain did not distinguish between both groups (FIG. 8B-E). Although in patients that were discharged from ICU, the SOFA-Score was significantly lower than in patients with fatal outcome, this parameter does not have the power to fully separate both groups (FIG. 8F).

TABLE 4

Patient data.

| ID | | PLT-count [1/nL] | MPV [fL] | SOFA-Score | Flow-Cytometry | Aggregometry | Molecular analysis | Additional Assays |
|---|---|---|---|---|---|---|---|---|
| 21 | I | 168 | 10.3 | 11 | + | | | E |
| | II | 101 | 10.4 | 9 | + | | | E |
| | III | 97 | 10.4 | 4 | + | $C^{Lo}$ | pTyr | E |
| 22 | I | 376 | 10.1 | 8 | + | | pTyr | E |
| | II | 72 | 12.3 | 10 | + | | | E |
| | III | | | | | Death | | |
| 23 | I | 44 | 11.8 | 14 | + | | | E |
| | II | 13 | 14.0 | 12 | + | | | E |
| | III | 231 | 11.3 | 8 | + | | | E |
| 24 | I | 303 | 11.9 | 11 | + | $C^{Lo}$, T | pTyr | |
| | II | 228 | 12.2 | 15 | + | $C^{Lo}$, T | pTyr | |
| | III | 283 | 11.8 | 8 | + | $C^{Lo}$, T, R, $C^{Hi}$ | pTyr | |
| 25 | I | 117 | 11-5 | 14 | + | $C^{Lo}$, T, R | pTyr, | E, P |
| | II | 109 | 11-3 | 9 | + | $C^{Lo}$, T, R, $C^{Hi}$ | pTyr | E, P |
| | III | 196 | 9.8 | 4 | + | | | E, P |
| 26 | I | 169 | 11.2 | 7 | + | $C^{Lo}$, R | pTyr, pSyk, Syk, pLAT | E, P |
| | II | 38 | 13.1 | 10 | + | | | E, P |
| | III | | | | | Death | | |
| 27 | I | 142 | 11.5 | 8 | + | $C^{Lo}$, T, R, $C^{Hi}$ | pTyr, pSyk, Syk, pLAT, GPVI, $pSHP_1$, $SHP_1$, $pSHP_2$, $SHP_2$ | E, P |
| | II | 82 | 12.2 | 8 | + | $C^{Lo}$ | pTyr | E, P |
| | III | 164 | 10.3 | 4 | + | $C^{Lo}$, T, R, $C^{Hi}$ | pTyr, GPVI | E, P |
| 28 | I | 179 | 10.8 | 9 | + | $C^{Lo}$, T, R, $C^{Hi}$ | pTyr, pSyk, Syk, pLAT, GPVI, $pSHP_1$, $SHP_1$ | E |
| | II | 131 | 11.2 | 5 | + | $C^{Lo}$, T, R | pTyr, GPVI | E |
| | III | 218 | 10.7 | 6 | + | $C^{Lo}$, T, R, $C^{Hi}$ | pTyr, GPVI | E |
| 29 | I | 39 | 12.8 | 13 | ++ | | | E |
| | II | 57 | 12.0 | 10 | ++ | $C^{Lo}$ | | E |
| | III | | | | | Death | | |
| 30 | I | 128 | 11.0 | 10 | +++ | $C^{Lo}$, T | pTyr, pSyk, Syk, pLat, $pSHP_1$, $SHP_1$, $pSHP_2$, $SHP_2$ | E, B |
| | II | | | | | Death | | |
| 31 | I | 284 | 11.1 | 8 | +++ | $C^{Lo}$, T, R, $C^{Hi}$ | pTyr, $pSHP_2$, $SHP_2$ | E, B |
| | II | | | | | Death | | |
| 32 | I | 167 | 10.7 | 5 | +++ | $C^{Lo}$, T, R | pTyr | E, P, B¶ |
| | II | | | | | Discharge | | |
| 33 | I | 217 | 11.9 | 10 | +++ | $C^{Lo}$, T, R | pTyr, $pSHP_1$, $SHP_1$, $pSHP_2$, $SHP_2$ | E, P, B |
| | II | 254 | 11.6 | 7 | +++ | $C^{Lo}$, T, R | pTyr | E, P, B |
| | III | | | | | | | |
| 34 | I | 97 | 12.5 | 8 | +++ | | | E, P, B |
| | II | | | | | Discharge | | |

TABLE 4-continued

Patient data.

| ID | | PLT-count [1/nL] | MPV [fL] | SOFA-Score | Flow-Cytometry | Aggregometry | Molecular analysis | Additional Assays |
|----|----|----|----|----|----|----|----|----|
| 35 | I | 369 | 12.6 | 9 | +++ | $C^{Lo}$, T, R, $C^{Hi}$ | pTyr | E, P |
| | II | 279 | 11.7 | 4 | +++ | $C^{Lo}$, T, R | pTyr | E, P, B |
| | III | | | | | Death | | |

FACS

+ : Receptor-Expression, Reticulated platelets, Platelets-reactivity-assays, Platelet-leucocyte-aggregates ++ : Including CLEC-2 receptor expression +++: Including CLEC-2 receptor expression and podoplanin-expression.

Aggregometry $C^{Lo}$: Stimulation with low dose CRP-X$_L$ [0.1 µg/ml]

$C^{Hi}$: Stimulation with high dose CRP-X$_L$ [1 µg/ml]

T : Stimulation with TRAP-6 [10 µM]

R : Stimulation with Rhodocytin [10 nM]

Additional Assays

E: IL-6-, TPO-, GPVI-Ectodomain-ELISA analysis

P: Plasma-incubation assays

B: Whole blood incubation assays

Example 3

During sepsis, patients may suffer from hemorrhagic diatheses, disseminated intravascular coagulation (DIC) and capillary leakage due to loss of vascular integrity. While all of these symptoms are associated with altered platelet function, the underlying cellular and molecular mechanisms are poorly defined. The only parameter currently integrated in clinical practice for sepsis evaluation is a reduced platelet count.

The present inventors herein disclose a comprehensive analysis of platelet function during sepsis progression on a molecular and cellular level and demonstrate that a reduced platelet GPVI reactivity is a promising biomarker for early sepsis diagnosis. The results of the present inventors reveal an unexpected uniform pattern of platelet hyporeactivity in all studied patients, regardless of potential confounders like age, focus of infection, isolated pathogens, or therapy.

Figure 2:
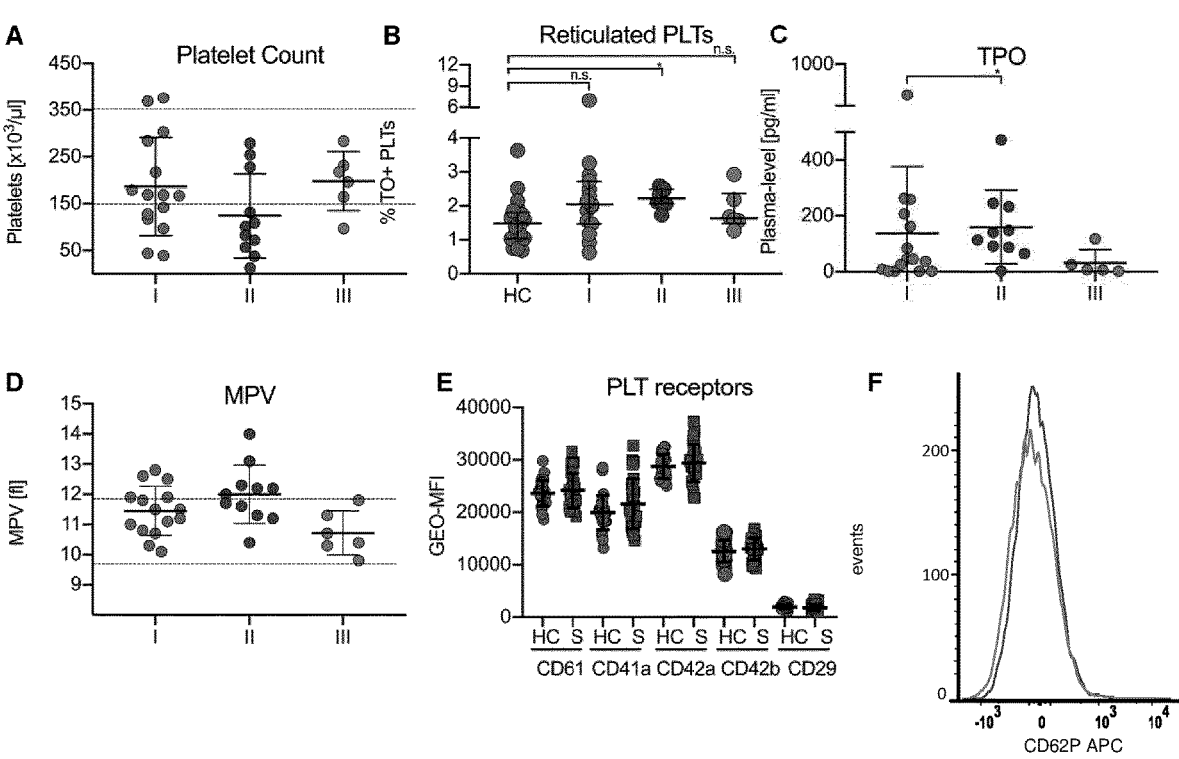
FIG. 2 shows that circulating platelets in sepsis are not pre-activated. Sepsis patient (S) characteristics are displayed at the following time points: I: admission day, II: day 5-7 and III: day of intensive care unit (ICU) discharge.
Figure 2:
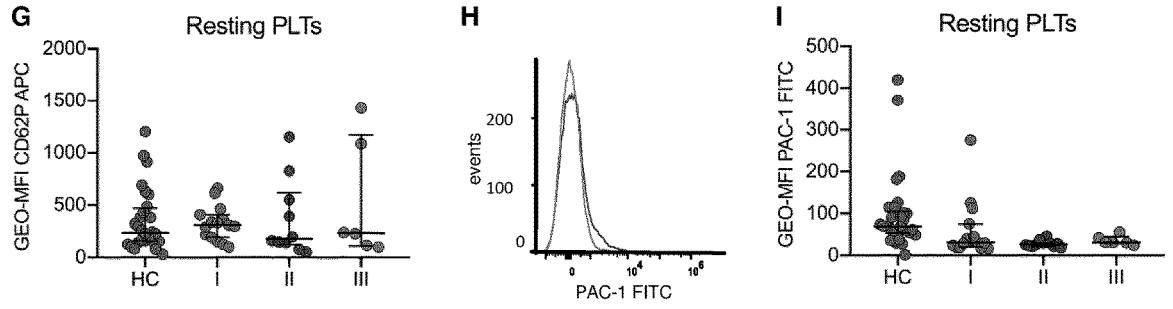

Hemorrhagic diathesis present in many sepsis patients is interconnected with a systemic microvascular coagulopathy, increased thrombin formation and a paradoxical thrombosis with increased bleeding risk. The presence of multiple triggers for platelet activation, however, did not result in detectable activation markers, as CD62P and PAC-1 binding were absent on circulating platelets in all patients of the cohort (FIG. 2).

Platelet function in a clinical setting is typically measured indirectly, for instance by in vitro bleeding time, using ADP/collagen or epinephrine/collagen cartridges in the Innovance® PFA-200. Moreover, platelet aggregometry is performed in diagnostic routine, using agonists like ADP, thrombin, or collagen. A precise platelet function analysis in these devices is hampered by thrombocytopenia or a reduced hematocrit, the present inventors thus have established, validated and applied a platelet function determination method that allows to detect defects in every patient, independent from any disruptive factor.

The present inventors found that hyporeactivity was most pronounced upon stimulation with the selective GPVI-agonist CRP-XL. A dysfunction of GPVI might contribute to the inflammatory immune response and progression into capillary leak syndrome. Dysfunction of CLEC-2-signaling, the second platelet (hem)-ITAM immunoreceptor on platelets, was found upon stimulation with the selective agonist rhodocytin (time point I: 5/8 patients). Platelets have a regulatory role in inflammatory processes and contribute to pathogen clearance. Detected hypo-responsiveness might be an actively regulated and inflammation-induced protective mechanism and could counteract platelet consumption in the periphery. Therefore, hampered GPVI-reactivity might be required, as several ligands for platelet GPVI binding and stimulation become expressed in response to vessel damage or inflammatory conditions occurring during sepsis like histones, fibrin or collagen (Claushuis 2018 Blood).

Platelets can interact with macrophages via CLEC-2 over increased podoplanin expression. However, the present inventors could not detect a significant increase in popdoplanin-expression on CD11b+/CD45+ myeloid cells in the study (FIG. 14). Nonetheless, platelet-leukocyte interaction was significantly increased in sepsis indicated by the ratio of CD41a+/CD45+ complexes (FIG. 14).

A microbe-dependent activation of platelets occurs to some extent. The present inventors were thus interested, whether the observed hyporeactivity to several agonists might be actively induced (or mediated) by the bacteria themselves. Surprisingly, none of the distinct blood-borne bacterial strains that were isolated from the patients could induce the hyporeactivity in platelets of healthy donors. Moreover, these strains failed to activate healthy platelets (in their own blood or plasma), implying that the bacteria themselves are not the key trigger for the finding. This finding is supported by fact that both, Gram-positive and -negative strains were used, while P. gingivalis as positive control activated platelets.

This suggests that the lowered platelet signaling strength is mediated by host-dependent signals and is most likely not related to microbes. The present inventors furthermore did not find any evidence that crossreaction of antimicrobial substances or other treatment modalities were accountable for this finding.

Hyporeactivity can be explained by GPVI ectodomain shedding, a mechanism that is physiologically involved in the regulation of signal-transduction in a broad variety of pathways. However, the present inventors did not find a correlation between GPVI receptor expression levels, GPVI ectodomain plasma levels and GPVI signaling strength, indicating that the observed signal defect is not due to GPVI receptor downregulation from the platelet surface.

Also, the increased levels of TPO, as well as the ratio and size of newly formed platelets point to an adequately enhanced biogenesis in response to sepsis-related thrombocytopenia. As the present inventors measured hyporeactivity homogenously in the complete platelet population already hours after disease onset, the present inventors consider the formation of defective platelets by bone marrow megakaryocytes in response to the disease condition as unlikely, although this mechanism has been described.

In 2016, the third international consensus definitions for sepsis and septic shock were published, modifying the so far existing definitions from 1992 and 2001. To ensure that the results are comparable to previously performed studies, the present inventors ensured that every included patient of their study was diagnosed according to both definitions.

As previously reported by others, stimulation of blood from healthy donors that has been experimentally thrombopenized revealed a decreased platelet reactivity in response to the thrombin peptide TRAP-6. Because of the low platelet count in sepsis patients, TRAP-6 was thus considered not suitable for whole blood stimulation assays in flow cytometry. Therefore, TRAP-6 was used only in healthy controls (having a regular platelet count) or in assays where the platelet count of patients has been adjusted.

The median age of the healthy donors is significantly lower than the age of patients in the cohort. To exclude an adverse effect of age on platelet function, a small cohort of elderly patients (mean age 67) was recruited during their routine check-up and performed platelet stimulation assays in comparison to a second group of younger controls (mean age 23.5). There were no differences detectable between both groups (FIG. 13), excluding a possible confounder just by age-difference.

Early diagnosis and immediate start of antibiotic therapy is crucial for patient survival. As an integral part of the SOFA-Score, low platelet count is an important laboratory finding for making sepsis diagnosis. But while the majority of the patients presented with inconspicuous platelet counts at ICU admission day (8/15), impaired GPVI reactivity is found multiple days earlier (93% already at ICU admission) and occurs reliably in every patient during disease progression. As affected platelet reactivity is already present at the first time point assessed in this study, the time-gap between the start of loss in platelet count and the begin in loss of reactivity might even be greater.

An advantage of a method according to the present invention is that it can be performed in a short period of time. Furthermore, an advantage of a method of the present invention is that it may be conducted in a fully automatized way and that only small amounts of whole blood (for example, 5 μL per test) are needed. Therefore, a method of platelet function testing of the present invention, such as by flow cytometry, can be well integrated in the clinical practice.

Besides CRP-XL, platelets also showed severe dysfunction upon stimulation with ADP which is commercially available and its stimulatory function is independent from a cross-linking process like for CRP-XL. Though, platelet reactivity upon ADP is affected by confounders, as P2Y12 receptor agonists (clopidogrel, prasugrel, thicagrelor, cangrelor), that are commonly used drugs and the difference in platelet activation between patients and healthy controls was lower compared to CRP-XL. Interestingly, aggregation upon CRP-XL stimulation increases according to an improved health state, whereas this tendency is not detectable in flow cytometry measurements in whole blood.

In conclusion, the present inventors demonstrate that platelet function and major immunoreceptor pathways are severely dysregulated during sepsis, which is useful in sepsis diagnostics. The present invention provides new means for diagnosing sepsis, such as sepsis complications like hemorrhagic diathesis and capillary leakage.

Example 4

Selectively testing platelet hyporeactivity via the GPVI signaling pathway after stimulation with CRP-XL and/or convulxin allows for an early detection of sepsis. The present invention thus provides valuable tools for early diagnosis of sepsis-specific impairment.

In the context of the Covid-19 pandemic, the present inventors performed comparable consecutive platelet function analyses for a period of 14 days with patients having a SARS-CoV-2 infection. In a cohort of 19 critically-ill patients with Covid-19 (that by these condition fulfill the Sepsis-3 criteria), the present inventors demonstrated that, in addition to the specific platelet hyporeactivity in response to CRP-XL stimulation (FIG. 16), the patients further showed a global hyporeactivity towards additional agonists such as ADP or the thrombin receptor agonist peptide TRAP-6 (FIG. 17). All patients in the cohort were at least temporarily supported by heart-lung-devices; all patients were ventilated. The data clearly show that platelet hyporeactivity correlates with disease severity. Furthermore, it is shown that, in its maximal manifestation, platelet hyporeactivity may lead to a systemic hyporeactivity, also referred to as an "exhausted platelet" phenotype.

The present inventors observed that the early signs of the impaired platelet function can be detected after stimulation with CRP-XL and/or convulxin. Stimulation with CRP-XL and/or convulxin thus allows for an early diagnosis of sepsis-specific impairment. Conclusively, stimulation with CRP-XL and/or convulxin for platelet function testing enables an early diagnosis of sepsis prior to a multi-organ failure, and is thus advantageous over prior diagnostic approaches since it allows for diagnosis in an earlier stage of the disease.

REFERENCES

ANDRES O., SCHULZE H., SPEER C. P. 2015. Platelets in neonates: central mediators in haemostasis, antimicrobial defence and inflammation. Thromb Haemost, 113(1):3-12.

BOULAFTALI, Y., HESS, P. R., GETZ, T. M., CHOLKA, A., STOLLA, M., et al. 2013. Platelet ITAM signaling is critical for vascular integrity in inflammation. J Clin Invest, 123, 908-16.

CLAUSHUIS, T. A. M., DE VOS, A. F., NIESWANDT, B., BOON, L., ROELOFS, J., et al. 2018. Platelet glycoprotein VI aids in local immunity during pneumonia-derived sepsis caused by gram-negative bacteria. Blood, 131, 864-876.

HITCHCOCK, J. R., COOK, C. N., BOBAT, S., ROSS, E. A., FLORES-LANGARICA, A., et al. 2015. Inflammation drives thrombosis after Salmonella infection via CLEC-2 on platelets. J Clin Invest, 125, 4429-46.

MALLOUKA et al. 2018. Assessment of a flow cytometry technique for studying signaling pathways in platelets: Monitoring of VASP phosphorylation inclinical samples. Practical Laboratory Medicine.

RAYES, J., LAX, S., WICHAIYO, S., WATSON, S. K., DI, Y., et al. 2017. The podoplanin-CLEC-2 axis inhibits inflammation in sepsis. Nat Commun, 8, 2239.

SPURGEON et al. 2014. Multiplexed phosphospecific flow cytometry enables largescale signaling profiling and drug screening in blood platelets. Journal of Thrombosis and Hemostasis.
WALLER, A. K., LANTOS, L., SAMMUT, A., SALGIN, B., MCKINNEY, H. et al. 2019. Flow cytometry for near-patient testing in premature neonates reveals variation in platelet function: a novel approach to guide platelet transfusion. Pediatric Research 85, 874-884.

WOTH, G. L. 2013. Platelet and platelet-derived microparticle studies in severe sepsis. PH.D. Thesis, University of Pecs.

The features of the present invention disclosed in the specification, the claims, and/or in the accompanying figures may, both separately and in any combination thereof, be material for realizing the invention in various forms thereof.

The invention claimed is:

1. A method of early detection and diagnosis of a human sepsis, comprising the following steps:
   a) providing a blood sample of a patient, wherein said blood sample is a whole blood sample, a platelet-rich plasma sample, a platelet suspension, or a platelet pellet,
   b) stimulating a platelet-specific (hem-)immunoreceptor tyrosine-based activation motif ((hem-)ITAM receptor by adding a (hem-)ITAM receptor agonistic agent to said sample, wherein said agonistic agent comprises collagen-related peptide cross-linked (CRP-XL) and/or convulxin,
   c) measuring a platelet function level,
   wherein said patient has an age of >1 year;
wherein said platelet function level is characterized by at least one parameter selected from the group consisting of a surface presentation of P-selectin, an activated integrin $\alpha IIb/\beta 3$, a platelet aggregation, a mepacrine uptake/release, and a phosphorylation status of Syk, LAT, SHP-1, SHP-2, $Fc R\gamma$, and $PLC\gamma 2$ or a combination thereof;
wherein the platelet function level measured is compared to a reference value and/or a reference sample of a healthy person not suffering from sepsis; and
wherein said method further comprises a step of determining that a patient has the sepsis or is at risk of developing the sepsis, if the platelet function level in said patient is decreased compared to the reference value and/or the reference sample.

2. The method according to claim 1, wherein said agonistic agent comprises both CRP-XL and convulxin.

3. The method according to claim 1, wherein said method is used for an early diagnosis of the sepsis.

4. The method according to claim 1, wherein said measuring is performed by a method selected from flow cytometry, aggregometry, detection and quantification of nucleic acids by polymerase chain reaction (PCR) or real time (quantitative) qPCR, enzyme-linked immunosorbent assay (ELISA), western blot, chromatography, and mepacrine assay.

5. The method according to claim 4, wherein said aggregometry is performed by any of light transmission aggregometry, impedance aggregometry, multiple electrode aggregometry, lumino-aggregometry, and microscale aggregometry, wherein a decreased aggregation of platelets is an indicator for sepsis, compared to a reference value and/or a reference sample of a healthy person not suffering from sepsis.

6. The method according to claim 1, wherein said measuring is performed by means of:
   i) a flow cytometric analysis of the surface presentation of P-selectin, and/or of the activated integrin $\alpha IIb/\beta 3$, and/or mepacrine uptake/release, and/or
   ii) an aggregometry, and/or
   iii) a quantification of the phosphorylation status of Syk, LAT, SHP-1, SHP-2, $Fc R\gamma$, and/or $PLC\gamma 2$.

7. The method according to claim 6, wherein said measuring is performed by means of i), ii), and iii).

8. The method according to claim 6,
   wherein said flow cytometric analysis of the surface presentation of P-selectin is performed using an antibody against a P-selectin, and/or wherein said flow cytometric analysis of the activated integrin $\alpha IIb/\beta 3$ is performed using an antibody against an activated conformation of integrin $\alpha IIb/\beta 3$, by fluorophore-conjugated fibrinogen,
wherein a decreased binding of said antibody against P-selectin and/or said antibody against an activated conformation of integrin $\alpha IIb/\beta 3$ is an indicator for sepsis, compared to a reference value and/or a reference sample of a healthy person not suffering from sepsis.

9. The method according to claim 8, wherein the antibody against a P-selectin is an anti-CD62P antibody.

10. The method according to claim 6, wherein said quantification of the phosphorylation status is performed by western blot using an antibody against phosphorylated Syk, phosphorylated LAT, phosphorylated SHP-1, phosphorylated SHP-2a, phosphorylated $Fc R\gamma$, and/or phosphorylated $PLC\gamma 2$, wherein a hypophosphorylation is an indicator for sepsis, compared to a reference value and/or a reference sample of a healthy person not suffering from sepsis.

11. The method according to claim 1, wherein said method is used for monitoring a patient's health condition,
   wherein said monitoring comprises performing steps a)-c) at a time point $t_1$ and a time point $t_2$, or
   wherein said monitoring comprises performing step a) at a time point $t_1$ and a time point $t_2$, and performing steps b)-c) subsequent to performing said step a) at said time point $t_2$,
   wherein said time point $t_2$ is after said time point $t_1$.

12. The method according to claim 11, wherein an increase in the platelet function level from said time point $t_1$ compared to the platelet function level from said time point $t_2$ indicates an amelioration of the patient's health condition or wherein a decrease in the platelet function level from said time point $t_1$ compared to the platelet function level from said time point $t_2$ indicates a worsening of the patient's health condition.

13. The method according to claim 11, wherein a time interval between said time point $t_1$ and said time point $t_2$ is between 6 h and 7 days.

14. A kit for diagnosing a human sepsis comprising:
   an agonistic agent for stimulating a platelet-specific (hem-)ITAM receptor, said agonistic agent comprising CRP-XL and/or convulxin,
   auxiliary compounds for performing the method as defined in claim 1,
   optionally comprising instructions for comparing a platelet function level of a patient to a reference value and/or a reference sample of a healthy person not suffering from sepsis, wherein a decrease in the platelet function level of the patient compared to the reference value and/or the reference sample indicates a human sepsis.

15. A method for diagnosing a human sepsis, wherein said method comprises the use of a kit comprising:
   an agonistic agent for stimulating a platelet-specific (hem-)ITAM receptor, said agonistic agent comprising CRP-XL and/or convulxin,
   auxiliary compounds for performing the method as defined in claim 1.

* * * * *